United States Patent
Li et al.

(10) Patent No.: US 9,709,584 B2
(45) Date of Patent: Jul. 18, 2017

(54) SYSTEM FOR PCR SAMPLE PREPARATION AND FOR PCR SET-UP

(71) Applicant: VELA OPERATIONS SINGAPORE PTE. LTD., Singapore (SG)

(72) Inventors: Xi Li, Singapore (SG); Quan Yuan, Singapore (SG); Yin Kum Ng, Singapore (SG)

(73) Assignee: VELA OPERATIONS SINGAPORE PTE. LTD., Singapore (SG)

( * ) Notice: Subject to any disclaimer, the term of this patent is extended or adjusted under 35 U.S.C. 154(b) by 131 days.

(21) Appl. No.: 14/402,908

(22) PCT Filed: May 23, 2013

(86) PCT No.: PCT/IB2013/054265
§ 371 (c)(1),
(2) Date: Nov. 21, 2014

(87) PCT Pub. No.: WO2013/175425
PCT Pub. Date: Nov. 28, 2013

(65) Prior Publication Data
US 2015/0168434 A1 Jun. 18, 2015

(30) Foreign Application Priority Data
May 24, 2012 (GB) .................................. 1209136.9

(51) Int. Cl.
| | | |
|---|---|---|
| *G01N 35/02* | (2006.01) | |
| *B01L 7/00* | (2006.01) | |
| *B01L 9/06* | (2006.01) | |
| *C12Q 1/68* | (2006.01) | |
| *G01N 35/10* | (2006.01) | |
| *G01N 35/00* | (2006.01) | |
| *G01N 35/04* | (2006.01) | |

(52) U.S. Cl.
CPC .............. *G01N 35/026* (2013.01); *B01L 7/52* (2013.01); *B01L 9/06* (2013.01); *C12Q 1/686* (2013.01); *G01N 35/00732* (2013.01); *G01N 35/025* (2013.01); *G01N 35/04* (2013.01); *G01N 35/10* (2013.01); *B01L 2300/0803* (2013.01); *B01L 2300/0829* (2013.01); *G01N 2035/00287* (2013.01); *G01N 2035/00366* (2013.01); *G01N 2035/00772* (2013.01); *G01N 2035/00811* (2013.01); *G01N 2035/0465* (2013.01)

(58) Field of Classification Search
CPC ..... B01L 2300/0803; B01L 2300/0829; B01L 7/52; B01L 9/06; C12Q 1/686; G01N 2035/00287; G01N 2035/00366; G01N 2035/00772
See application file for complete search history.

(56) References Cited

U.S. PATENT DOCUMENTS

| | | | |
|---|---|---|---|
| 2003/0211595 A1 | 11/2003 | Lee | |
| 2009/0136386 A1* | 5/2009 | Duffy | ..................... B01L 9/527 422/400 |
| 2009/0155123 A1 | 6/2009 | Williams et al. | |

FOREIGN PATENT DOCUMENTS

| | | |
|---|---|---|
| CN | 101522909 A | 9/2009 |
| CN | 102147406 A | 8/2011 |
| DE | 4406107 C1 | 5/1995 |
| EP | 1102068 A1 | 5/2001 |

OTHER PUBLICATIONS

International Search Report and Written Opinion for Application No. PCT/IB2013/054265 dated Nov. 6, 2013.
Search Report for Application No. GB 1209136.9 dated Sep. 21, 2012.
Chinese Patent Application No. 201510683429X Office Action dated Feb. 24, 2017.

* cited by examiner

*Primary Examiner* — Cynthia B Wilder
(74) *Attorney, Agent, or Firm* — Hanh Loeser & Parks, LLP—San Diego

(57) ABSTRACT

A method of setting up a polymerase chain reaction ("PCR") includes providing a loading device configured to receive sample tubes for setting up a PCR; providing a tube holding device comprising at least a first receiving opening; attaching the tube holding device to the loading device; and aligning at least one receiving opening of the tube holding device with one of the first and second receiving openings of the loading device and simultaneously covering the other of the first and the second receiving openings of the loading device.

15 Claims, 19 Drawing Sheets

SYSTEM FOR PCR SAMPLE PREPARATION AND FOR PCR SET-UP

CROSS REFERENCE TO RELATED APPLICATIONS

The present application is a national phase entry under 35 U.S.C. §371 of International Application No. PCT/IB2013/054265, filed May 23, 2013, published in English, which claims the benefit of and priority to GB Patent Application No. 1209136.9, filed May 24, 2012, all of which are hereby incorporated by reference.

FIELD OF THE INVENTION

The present invention relates to molecular diagnostics. In particular, the present invention relates to a system for PCR sample preparation and for PCR set-up, a method of preparing a PCR, and the use of a tube holding device for PCR set-up.

BACKGROUND OF THE INVENTION

The polymerase chain reaction (PCR) enables researchers to produce large quantities a specific DNA sequence for further analysis in a relatively short time frame. PCR is nowadays a preferred methodology in research applications and in the detection of presence or absence of a target molecule, e.g. in clinical and diagnostic applications.

Technical progress has lead to compact benchtop instruments that enable automated high-precision PCR set-ups. Robotic liquid handling systems have been automated for the PCR set-up. Further, also processes preceding the PCR set-up have been automated, e.g. the extraction and purification of nucleic acid material from sample to be investigated, e.g. clinical samples, environmental samples, material for forensic medicine, etc. The automatization of these processes has lead to a reduction of costs due to lab personnel, and played a role in avoiding human errors leading to contamination of the devices and reagents, wrong pipetting steps and consequently incorrect results, etc.

There is, however, a permanent need to improve these methods and devices in order to eliminate any potential risk of contamination and/or misleading results as well as to accelerate existing methods to safe resources and time.

SUMMARY OF THE INVENTION

There is a need to provide for an improved PCR sample preparation, e.g., the extraction of nucleic acids from a sample to be investigated, and/or for an improved PCR set-up.

The object of the present invention is solved by the subject-matter of the independent claims. Further embodiments and advantages of the invention are incorporated in the dependent claims.

The described embodiments similarly pertain to the system for PCR sample preparation and PCR set-up, the method of preparing a PCR, and the use of a tube holding device. Synergetic effects may arise from different combinations of the embodiments although they might not be described in detail hereinafter.

Furthermore, it shall be noted that all embodiments of the present invention concerning a method might be carried out with the order of the steps as described. Nevertheless, this has not to be the only and essential order of the steps of the method of the present invention. The skilled person gathers all kinds of different orders and combinations of the method steps described herein, unless explicitly mentioned to the contrary hereinafter.

According to an exemplary embodiment of the invention, a system for PCR sample preparation and for PCR set-up is presented. The system comprises a loading device for receiving tubes. Hereinbelow tubes are generally referred to as "sample tubes", designating any type of vessel that is suited for taking up liquids and/or solids used in preparing or setting up PCR. The loading device comprises a first receiving section, and the first receiving section comprises at least a first receiving opening and a second receiving opening. Furthermore, the first receiving opening and the second receiving opening are adapted to respectively receive a sample tube. The system further comprises a tube holding device for being attached to the loading device.

In other words, the loading device and the tube holding device are configured in combination such that an attachment, a fixation, and/or a mounting of the tube holding device at or to the loading device is facilitated. The attachment between the loading device and the tube holding device is provided such that a fully automated PCR set-up and PCR sample preparation for the subsequent PCR is facilitated by the presented system. For the purpose of the attachment, fastening means or attachment means like protrusions, threads, or cooperative engaging means may be provided at the loading device and/or the tube holding device such that the desired attachment is achieved. This will be described in more detail hereinafter.

The provision of the tube holding device allows the user to cover unused tube positions, i.e. the unused receiving openings, of the loading device. The loading device may be embodied for example as a thermorack, e.g., a thermorack rotor disk, which may be used during the fully automated PCR set-up. Furthermore, the combination of the tube holding device and the loading device provides for the possibility of indicating assay specific reagent types by indicators or coding elements, like e.g. color labels or color indications, which according to the present invention, can be provided at the tube holding device. The use of specific coding elements on the tube holding device increases the practicability for the user and further increases the reliability of the PCR process. In particular, a failsafe mechanism is presented, such that the user places the sample tubes at the correct position. In other words, the presented system assists the user or a device in placing the sample tube at the correct position in the loading device. Additionally, the provision of the tube holding device in combination with the loading device facilitates a simultaneous placement and/or simultaneous removal of all tubes that are to be positioned at the loading device. This may accelerate the PCR sample preparation and PCR set-up process to a large extent.

The previously described advantages of the aspect of covering parts of the loading device of the present invention, the aspect of indicating by means of coding elements of the present invention, and the aspect of enabling for simultaneous placement and removal of a plurality sample tubes may especially provide for advantages during PCR sample preparation and PCR set-up when the loading device is embodied as a thermorack rotor and a correspondingly adapted tube holding device. The tube holding device may have an assay specific amount of receiving openings, which are positioned assay specific and which may comprise an assay specific coding elements for the sample tubes which are to be inserted into the arrangement.

The tube holding device may thus provide for a double functionality, as will be described hereinafter. First, the tube holding device may be configured to removeably attach the sample tube or tubes which are used for PCR sample preparation and for PCR set-up, such that the inserted sample tubes can be positioned and moved by means of moving the tube holding device. Second, the tube holding device may provide for a cover functionality, as the areas of the tube holder device between the receiving openings may be advantageously used to cover and/or close receiving openings of the loading device which in particular cases may not be used.

It should be noted that in this and every other exemplary embodiment, the tube holding device may comprise a plurality of receiving openings, and the loading device may also comprise a plurality of receiving openings larger than two. This provides for a system with increased possibilities of choosing between various numbers of different assays that can be performed in combination with assay specific tube holder devices. This leads to different possibilities of advantageous pipetting paths for the automated system or the user. Due to the large number of the receiving openings of the loading device and of the tube holding device, optimized selections of uncovered receiving openings is facilitated such that optimized pipetting paths from sample tubes in the receiving openings to PCR reaction chambers are facilitated. This will be explained in more detail with respect to the following FIGS. 1 to 7, in which specific pipetting paths are described, such that the user gathers from the advantageous selection of receiving openings by combining the loading device with the assay specific tube holding device.

The presented system may provide for the advantage of pipetting directly into the second receiving section of the loading device, where PCR reaction chambers can be provided. In case the loading device is embodied as a thermorack rotor, pipetting directly into the rotor is facilitated by the present invention. This may be gathered from e.g. FIG. 1. Furthermore, simultaneous extraction set-up of e.g. four different assays may be facilitated by the presented system. In addition, simultaneous extraction of RNA and DNA in the same run is facilitated by the combination of the loading device and the tube holding device according to the present invention.

According to another exemplary embodiment of the invention, the system comprises one loading device and a plurality of different, assay specific tube holder devices.

A reservoir of different tube holder devices may be comprised by the presented system.

According to another exemplary embodiment of the invention, the tube holding device is a tube holding plate.

If desired, the tube holding plate may be embodied with an essentially circular shape. However, other shapes like rectangular or quadratic shapes may be possible embodiments of the tube holding plate. Furthermore, the tube holding device may be formed out of a metal or an alloy, but also polymer materials or other materials which are suitable for producing such a tube holding device may be used.

According to another exemplary embodiment of the invention, the tube holding device comprises at least a first receiving opening. Further, the tube holding device is attachable to the loading device such that the receiving opening of the tube holding device is aligned with at least one of the first receiving opening and the second receiving opening of the loading device and simultaneously covers the other of the first and the second receiving openings of the loading device.

Thus, in the attached configuration at least one receiving opening is covered and one is uncovered. In other words, this embodiment facilitates to cover, overcast and/or blanket the receiving openings of the loading device which are not used according to the intended assay and/or according to corresponding pipetting path performed by an automated pipetting device, which aspect of the present invention will be described in more detail. The loading device and the assay specific tube holding device can be arranged together such that the tube holding device covers and/or blankets the unused receiving opening of the loading device. The combination further facilitates that alignment of the receiving opening of the tube holding device is achieved with one of the receiving openings of the loading device. Due to this alignment, a sample tube according to a specific assay can be placed or inserted via the two aligned receiving openings, and can thereby be placed into the loading device for the subsequent PCR sample preparation and PCR set-up. In other words, by attaching the tube holding device to the loading device, a selection of the plurality of receiving openings of the loading device is performed. Only those receiving openings of the loading devices are not covered by the tube holding device which receiving openings are to be used according to the presently used or desired assay.

This selection provides for an improved usability for the lab personnel and further provides for a simplification for the PCR sample preparation and for the PCR set-up.

According to another exemplary embodiment of the invention, the system comprises at least one a sample tube, wherein the sample tube is removeably attached to the receiving opening of the tube holding device.

In other words, the system provides for a tube holding device which is configured such that one or more sample tubes are moveable and receivable by the loading device and the tube holding device by aligning the opening of the tube holding device with one of the first and the second receiving openings of the loading device. Consequently, the sample tube, which is received, is held by the tube holding device is attached thereto such that the tube is moveable by moving the tube holding device. By attaching the tube holding device to the loading device, the held sample tube is inserted into the loading device. For the purpose of attaching the sample tube to the tube holding device, fixation or fastening means may be provided at the tube holding device and/or the sample tube. For example, purely mechanical means and forces may be used by means of an engagement of the collar of the sample tube with the circumferential surface of a receiving opening of the tube holding device. A corresponding provision or adaptation of the entangled diameters of the receiving openings and of the sample tube may be seen as another aspect of the present invention. For example, the sample tube may be received by the tube holding device in a hanging position in the receiving opening, as can be gathered from FIG. 8, for example. However, also other fastening and attaching means may be provided by the present invention, like for example magnetic forces, in order to attach the sample tube to the tube holding device. As a further embodiment, corresponding protrusions or threads may be used in order to engage the sample tube and the tube holding device for the desired removable attachment, which can be released again, if desired.

According to another exemplary embodiment of the invention, the first receiving section of the loading device comprises a first plurality of receiving openings for receiving a sample tube, and the tube holding device comprises a second plurality of receiving openings for receiving a sample tube. Furthermore, in the attached position of the tube holding device at the loading device a part of the receiving openings of the loading device are aligned with corresponding receiving openings of the tube holding device and a remaining part of the receiving openings of the loading device are covered by the tube holding device.

This embodiment can easily be gathered from, for example, FIGS. 1, 8, and the sequence of FIGS. 13 to 15, where one loading device with three different tube holding plates for three different assays are shown.

According to another exemplary embodiment of the invention, a first plurality of sample tubes positioned for a first PCR assay is comprised, and a second plurality of sample tubes positioned for a second PCR assay is comprised by the system. Furthermore, the tube holding device comprises one receiving opening for each sample tube such that all sample tubes are removeably attached to the tube holding device by means of the respective receiving opening for the tube holding device.

In other words, the tube holding device provides for two more or less separated sections or segments by means of which the sample tubes of the first assay or for the first assay are separated from the sample tubes for the second assay. In principle, this may be scaled up to each plurality of PCR assays, like for example a third plurality of sample tubes for a third PCR assay, a fourth plurality of sample tubes for a fourth PCR assay, a fifth plurality of sample tubes for a fifth PCR assay, and so on. The scope of this embodiment shall not be limited to the recitation of the fifth PCR assay, but may be extended up to larger numbers if desired by the user. Therefore, by means of the combination of the loading device and the design of the tube holding device, all needed and different sample tubes for a plurality of PCR assays can simultaneously be inserted in the loading device and/or can simultaneously be removed, i.e. at once, from the loading device. This may accelerate the procedure of PCR sample preparation and PCR set-up.

According to another exemplary embodiment of the invention, a diameter of the receiving openings of the tube holding device is larger than a diameter of the sample tube, and wherein the diameter of the receiving openings of the tube holding device is smaller than a diameter of a collar of the sample tube.

This embodiment facilitates by means of gravitational forces only, that the tubes are hanging in the tube holding device due to an engagement between the rims of the receiving openings and the collars of the tubes. Therein, the rims may be provided by the circumferential surface of the openings of the tube holding device. If desired, additional rim elements may be provided such that a strengthened engagement between the tubes and the tube holding device is realized. Further aspects about the diameter combination of the receiving openings and the sample tubes used according to the present invention for PCR sample preparation and PCR set-up will be described with respect to FIG. 2 hereinafter.

According to another exemplary embodiment of the invention, the tube holding device comprises a coding element for coding information regarding an intended PCR-related purpose of the receiving opening A coding element may be seen as an element of the system which is configured to provide for information, like e.g. mechanical, optical, electronical or magnetical information to a user or a device about the respective receiving opening of the assay specific tube holder device. This information may be detected by a mechanical, optical, electronical or magnetical read out device, like e.g. a colour code scanner, of the presented system. In addition, abbreviations can be comprised as coding element at a receiving opening of the tube holder device. A coding element may for example be a mechanical pattern like differently shaped lines at or around a receiving opening. This may be gathered from FIG. 1 or 2 for example. A coding element may also be a chip which can be read out electronically or may be a colour code, like a colored surface. Further, text or abbreviations may be used to indicate to the user, which sample has to be positioned at the respective receiving opening.

The system may provide for sensing technologies which allows for recognizing the coding element and/or allows for reading out the information. By performing for example a color comparison between a color code on the tube holding device and a color code on a plurality of sample tubes, the correct sample tube may be selected based on the color comparison. Subsequently, the selected sample tube may be inserted into the corresponding receiving opening having the same color as the coding element.

According to another exemplary embodiment of the invention, the tube holding device comprises a coding element at each receiving opening for indicating which substance is to be positioned in the respective receiving opening by means of the sample tube.

According to another exemplary embodiment of the invention the coding element is a color code.

The color codes may also be seen as labels on the tube holding device to indicate the reagent type of each position, i. e. of each receiving opening, of the tube holding device. This embodiment of the tube holding device may prevent misplacing the tubes to wrong locations. For example, the color code may be provided as a color coded ring around a receiving opening. The PCR-related purpose indicated by means of the coding element may for example be "water", "positive control", "primer and probe mixture (PPM)", "extraction control primer and probe mixture (ECPPM)", "quantitative standard (QS)". However, also other indications may be used without departing from the scope of the present invention. In addition to colour codes, abbreviations can be comprised at each receiving opening of the tube holder device.

According to another exemplary embodiment of the invention, a color code is a colored surface of the tube holding device, and wherein the colored surface is close to or at the respective receiving opening. This embodiment may be gathered for example from the following FIGS. 1 and 9.

According to another exemplary embodiment of the invention, the loading device is a PCR thermorack.

The PCR thermorack may be inserted into a thermocycler after the PCR sample preparation and PCR set-up has been performed by means of the presented system. As can be gathered from FIG. 17, the PCR reaction chambers which have been prepared during the PCR set-up process can directly be inserted by means of the loading device into a foil sealing device. Also fast and direct insertion into a thermocycler, in particular a PCR thermocycler, or also into an autoclaving device is facilitated by the presented loading device.

According to another exemplary embodiment, the loading device and the tube holding device have both a circular shape.

Consequently, a circular arrangement of PCR reaction chambers may be placed around the loading device, such that pipetting from the central part of the circular-shaped loading device towards the circumferential region of the loading device and into the PCR reaction chambers positioned there is facilitated.

According to another exemplary embodiment of the invention, the loading device comprises a second receiving section for receiving a plurality of PCR reaction chambers.

Such reaction chambers for PCR reagents may be gathered from, for example, FIGS. 1, 5, 8, and 13. Such PCR reaction chambers may also be comprised by the system according to the present invention. The PCR set-up may be performed such that the desired liquid combination is provided within the PCR reaction chambers by pipetting the necessary reagents from the sample tube into the PCR reaction chambers. The combination of the tube holding device and the loading device allows for optimized pipetting paths, which will be explained in more detail for example with respect to following FIGS. 5 and 7. As a further embodiment, the second receiving section may be a circumferential section around the first receiving section of the loading device. This may be gathered from for example FIG. 1.

According to another exemplary embodiment of the invention, the tube holding device expands horizontally along a first plane, wherein the first plane has a circular shape and cover a circular area of the loading device with the exception of at least one receiving opening of the loading device which is aligned with one of the receiving openings of the tube holding device.

In principle, a plurality of aligned receiving openings and a plurality of covered receiving openings can be realized by the attachment of the tube holder device to the loading device according to the present invention. Starting from this, the person skilled in the art is clearly aware of how to geometrically configure the tube holding device in order to cover specific receiving openings of the loading device, whereas simultaneously other receiving openings are released, unblocked or uncovered for being able to receive a sample tube.

According to another exemplary embodiment of the invention, the tube holding device comprises a handle for being grasped by a user. The handle facilitates inserting and/or removing the tube holding device into and/or from the loading device.

In order to facilitate and/or accelerate a fully automated PCR sample preparation and PCR set-up, an automatic exchange of assay specific tube holding devices is provided by the present invention. A grasping unit may be configured to exchange several assay specific tube holding devices and engage and disengage them respectively with the used loading device. A reservoir of different tube holder devices may be comprised by the presented system.

According to another exemplary embodiment of the invention, the tube holding device comprises a first surface segment of a first PCR assay, and comprises a second surface of a second PCR assay. The first surface segment comprises a plurality of receiving openings, and the second surface segment comprises a plurality of receiving openings. Therein, the first receiving opening and the second receiving opening, as defined previously, shall be understood to be comprised by the first and the second surface segment of the present embodiment. In other words, the tube holding device provides for two separated regions, wherein each region provides for the sample tubes necessary for providing all the reagents for a specific assay.

According to another exemplary embodiment of the invention, the first surface segment comprises at least one color code indicating a first color of a receiving opening, and the second surface segment comprises at least one color code indicating a color code of a receiving opening, wherein the first and the second colors are the same. In general, the first and second segments may comprise a coding element, as described herein.

According to another exemplary embodiment of the invention, the first and the second PCR assay segments of the tube holding device are arranged relative to each other in a geometrical manner which is chosen from the group comprising: the first segment is a first segment of circle and the second segment is a second segment of circle, the first and second segments are divided on the circular tube holding device by a straight line or by a curved line passing a centre of the circular tube holding device, the receiving openings of the first and the second segments are symmetric to a central point of the tube holding device, and any combination thereof.

For example, the straight division between the two segments may be gathered from FIG. 1, whereas the curved division between the first and second segments can be gathered from for example FIG. 2 and FIG. 11. The point-symmetric distribution of the assay specific receiving opening distribution as shown for example in FIG. 5 may provide for the possibility of improved pipetting paths, which is described in more detail with respect to FIG. 5.

According to another exemplary embodiment of the invention, each receiving opening of the tube holding device is marked with a color code.

According to another exemplary embodiment of the invention, the tube holding device comprises at least one attachment means for releasable attaching the tube holder device to the loading device.

Attachment means, like for example the use of magnetic forces or threads may be seen as in the scope of this exemplary embodiment.

According to another exemplary embodiment of the invention the attachment means is configured to be inserted into a receiving opening of the loading device to stabilize the attachment of the tube holding device at the loading device.

In another more specified embodiment, the attachment means may be seen as stabilizing protrusion elements. Engaging protrusions with corresponding engagement recesses, like e.g. receiving openings, at the loading device may be presented according to this exemplary embodiment.

According to another exemplary embodiment of the invention, the system comprises a cover which is configured for simultaneously covering the loading device and the tube holding device.

According to an even more specified embodiment, a system with the cover is autoclaveable and is easy to be decontaminated. Consequently, this embodiment presents an autoclaveable system with a cover, a loading device, and a tube holding device. The cover may be optically transparent or optically not transparent. The cover may prevent the cross carry over during a PCR sample preparation process in the presented system.

According to another exemplary embodiment of the invention, the cover has essentially a circular shape and is adapted to the shape of the tube holding device and/or the shape of the loading device.

According to another exemplary embodiment of the invention, the system comprises a scanner, wherein the scanner is configured for scanning at least one element chosen from the group comprising elution plate, extraction reagents, assay reagents, sample tubes, and any combination thereof. The scanner is configured to transmit scanned data to a calculating unit.

The scanner may be embodied as for example a handheld scanner. In particular, the scanner may be configured to scan barcodes used for transporting information. Therefore sample information can be gathered by the scanner via for example barcode scanning and may be transmitted to a calculating unit. The calculating unit may create data for a PCR thermocycler in a thermocycler readable data format. This may further accelerate the complete PCR procedure and may result in a high throughput system for the user.

According to another exemplary embodiment of the invention, the system may comprise the calculating unit which is configured to generate sample information in a thermocycler readable data format.

Thus, interfacing data between the system for PCR sample preparation and for PCR set-up one the one hand and the thermocycler on the other hand is also presented by the present invention.

According to another exemplary embodiment of the invention, the system comprises the thermocycler, wherein the thermocycler and the calculating unit are in communication with each other. The thermocycler is configured to automatically perform a PCR in a received PCR reaction chamber based on the sample information received in the thermocycler readable data format from the calculating unit.

Therein, wireless or wired communication between the thermocycler and the calculating unit may be used according to this embodiment of the present invention. A fully automated system providing PCR sample preparation, PCR set-up, and carrying out the complete PCR may thus be presented by the present invention.

According to another exemplary embodiment of the invention, the tube holding device is configured assay specific with respect to a geometrical distribution of the receiving openings.

According to another exemplary embodiment, the system comprises a first tube holding device and a second tube holding device, wherein the tube holding devices are configured assay specific respectively, and wherein the respective configuration of the first tube holding device is different from the second tube holding device with respect to the distribution of the receiving openings.

According to another exemplary embodiment of the invention, the first receiving section is centrally positioned at the loading device. Furthermore, the loading device is adapted to receive PCR reaction chambers at the second receiving section positioned exterior to or outside of the central position of the first receiving section. Furthermore, the tube holding device is configured for a specific assay with respect to the geometrical distribution of the receiving openings, such that straight pipetting paths from a receiving opening with a coding element for a sample tube containing a specific concentration of a target molecule into the second receiving section are facilitated. Furthermore, this embodiment facilitates that pipetting paths cross covered receiving openings of the loading device only.

As can be gathered from following FIG. 7, such a distribution of receiving openings of the tube holding device facilitates to use direct pipetting paths from the receiving openings towards a circumferential region of the tube holding device, whereby only covered sections of the below lying loading device are crossed. The pipetting paths are indicated in FIG. 7 by the dashed line arrows. This may further increase the security level of carrying out PCR sample preparation and PCR set-up with the presented system. Unused and covered receiving openings of the loading device are not contaminated during the pipetting procedure in case the pipetting paths are chosen as shown within FIG. 7.

According to another exemplary embodiment of the invention, the tube holding device comprises a plurality of receiving openings at which an intended receipt of a sample tube containing a specific concentration of a target molecule is indicated respectively. This may be true for at least a part of the plurality of receiving openings. The positions of the receiving openings is configured such that a path between a central region of the tube holding device and an edge region of the tube holding device crosses receiving openings, at which an intended receipt of a sample tube with a specific concentration of a target molecule is indicated, from low concentration to high concentration.

In the context of the present invention the term "edge region" shall not be understood such that an edge is necessarily comprised. An "edge region" may also be understood as a peripheral region or a boundary region.

For this and every other embodiment of the present invention such an indication may be done by a coding element, an abbreviation or a color code as described herein. This exemplary embodiment will be described in more detail with respect to the embodiment of FIG. 5. This embodiment may also advantageously decrease the contamination risk of a surface segment of the system of the present invention during a PCR set-up process.

According to another exemplary embodiment of the invention, the tube holding device comprises a first receiving opening at which an intended receipt of a sample tube with a first concentration of a target molecule is indicated. The tube holding device comprises a second receiving opening at which an intended receipt of a sample tube with a second concentration of a target molecule is indicated. Furthermore, the first and the second receiving openings are positioned relative to each other, such that straight pipetting paths from a central region to an edged region of the tube holding device are facilitated, which paths pass the first and second receiving openings from low to high concentrations.

Consequently, in a further exemplary embodiment of the invention, a first tube holding device is removed from the loading device and is replaced by a second loading device in order to facilitate a further PCR set-up with different requirements. Consequently, in this and every other exemplary embodiment of the invention, the loading device can be combined with a plurality of different tube holding devices.

According to another exemplary embodiment of the invention, a method of preparing a PCR is presented. The method comprises the steps of providing for a loading device, providing for a tube holder device and attaching the tube holder device to the loading device. Furthermore, the loading device configured for receiving sample tubes for setting up a PCR and the loading device comprises a first receiving section. The first receiving section comprises at least a first and a second receiving opening wherein the first receiving opening and the second receiving opening are adapted to respectively receive a sample tube.

According to another exemplary embodiment of the invention, the tube holder device comprises at least a first receiving opening. The method of this embodiment further comprises the step of aligning the receiving opening of the tube holder device with one of the first receiving opening and the second receiving opening of the loading device and thereby simultaneously covering the other of the first and the second receiving openings. The presented method of the present invention facilitates covering unused receiving sections by means of attaching the tube holder device to the loading device. Further, the method may make use of indicating assay specific reagent types by for example colored labels or by other color indicators. Combining the tube holder device with the loading device enables for simultaneous placement of sample tubes and enables for simultaneous removal of sample tubes in particular of all used tubes from the loading device.

According to another exemplary embodiment of the invention, method further comprises the steps of removably attaching a sample tube to the tube holding device and inserting the sample tube into a receiving opening of the loading device by attaching the tube holding device to the loading device.

In other words, the spatial distribution of the receiving openings of the tube holder device is adapted to the spatial distribution of the receiving openings of the loading device and is based on the requirements of the assay to which the tube holder plate is dedicated. The step of attaching may be done by a user or by an automated device.

According to another exemplary embodiment of the invention, the method further comprises the step of simultaneously separating the tube holder device and the sample tube received by the loading device from the loading device by grasping the tube holder device and removing the tube holder device from the loading device.

In other words, all sample tubes used within the loading device can be removed at once by grasping the tube holder device and moving it away from the loading device. Therefore, an improved placement automation is provided by the present invention.

According to another exemplary embodiment of the invention, the method comprises the step of simultaneously removing a first plurality of sample tubes for a first PCR assay and a second plurality of sample tubes for a second PCR assay from the loading device by grasping the tube holder device and removing the tube holder device from the loading device.

This embodiment emphasizes the high throughput abilities of the presented method, as a plurality of PCR assays may be prepared simultaneously and all needed sample tubes can be removed at once. This embodiment is not limited to a first and a second PCR assay but may be extended to a larger number of PCR assays.

According to another exemplary embodiment of the invention, the method comprises the step of inserting a stabilizing protrusion element of the tube holder device into a receiving opening of the loading device during attaching the tube holder device to the loading device.

In order to stabilize the attachment and/or fastening of the tube holder device at the loading device stabilizing protrusion elements may be used. As a general remark it should be noted, that general attachment means may be provided which during attaching the tube holder device to the loading device create the attachment via for example a integral connection, form closure or via for example threads or corresponding engaging elements.

According to another exemplary embodiment of the invention, the method comprises the step of covering unused receiving openings of the loading device by the tube holding device.

It may be seen as an important aspect of the invention that simultaneously another receiving opening than the covered receiving opening of the loading device is uncovered, i. e. aligned with a receiving opening of the tube holding device.

According to another exemplary embodiment of the invention, the tube holding device comprises at least a first opening having a color code indicating a first color and a second opening having a color code indicating a second color. The method of the presented embodiment comprises the steps of providing a sample tube with a color code indicating a third color, selecting the receiving opening of the tube holding device which has the same color as the color code of the sample tube and inserting the sample tube into the selected receiving opening of the tube holding device.

In other words, based on a color comparison, the correct receiving opening of the loading device for the process of sample preparation is identified.

According to another exemplary embodiment of the invention, the method comprises the step of covering the loading device and the tube holding device and inserted sample tubes by placing a cover to the loading device, the tube holding device, and the inserted sample tubes.

If desired, autoclavability can be reached by this covering process. In other words, the presented system can be placed in an autoclave to perform decontamination. If desired the loading device and the tube holding device and the cover can be configured to withstand high pressure of saturated steam at approximately 121° C. for around 15 to 20 minutes, which is typical for an autoclave.

According to another exemplary embodiment of the invention, the method comprises the step of scanning data of at least one element, chosen from the group comprising elution plate, extraction reagents, assay reagents, sample tubes, and any combination thereof. The method also comprises the step of transmitting the scanned data to a calculating unit for PCR purposes.

The system of the present invention is able to recognize and set-up the desired PCR reaction on the loading device to which the tube holding device has been arranged. A wireless or wirebound communication may be provided between a scanner, for example a handheld scanner, and a calculating unit which may be comprised by the system, or which may also be comprised by a computer which is in communication with the system of the present invention. The calculating unit in any case may be provided in communication with a thermocycler and which unit may generate sample information in a thermocycler readable data format. These data in the thermocycler readable data format may be transmitted to the thermocycler to initiate the PCR. Furthermore, performing a PCR in a received PCR reaction chamber by the thermocycler based on the sample information received in the thermocycler readable data format may be seen as another exemplary embodiment of the invention. Further aspects related to this embodiment may be gathered from FIGS. 19 and 20.

According to another exemplary embodiment of the invention, the method comprises the step of indicating at each receiving opening of the tube holding device which respective substance is to be positioned in the respective receiving opening.

This may be done by a coding element. This embodiment ensures that the assay specific configuration or adaption of a tube holding device is followed by the user. In particular, the user will recognize the indication provided at the tube holding device and can easily insert the corresponding sample tube into the receiving opening in a failsafe manner. In other words, a failsafe mechanism for the user is presented, by means of which the user is guided through the process of inserting all the necessary sample tubes into the loading device.

According to another exemplary embodiment of the invention, the first receiving section is centrally positioned at the loading device. This embodiment comprises the step of receiving PCR reaction chambers by the loading device at the second receiving section positioned exterior of the central position of the first receiving section. Furthermore, the presented method comprises the step of pipetting along a straight path from a receiving opening with an coding element for a sample tube containing a specific concentration of a target molecule into the second receiving section, which path crosses covered receiving openings of the loading device only.

This advantageous embodiment of the present invention may be gathered from following FIG. 7. The configuration of the receiving openings of the tube holding device is provided in such a way that the desired pipetting along the straight path towards the received PCR reaction chambers in the circumferential second section is facilitated.

According to another exemplary embodiment of the invention, the method comprises the steps of indicating at a plurality of the receiving openings of the tube holding device an intended receipt of a sample tube containing a specific concentration of a target molecule, respectively. Furthermore, the step of pipetting along a path between a central region of the tube holding device and an edged region of the tube holding device and thereby crossing receiving openings at which an intended receipt of a sample tube with a specific concentration of the target molecule is indicated is performed from low concentration to high concentration.

In other words, this method ensures that pipetting paths are chosen in combination with the underlying tube holding device with its assay specific opening distribution such that crossing a sample tube with a lower concentration of the target molecule compared to the concentration where the pipetting process started is avoided.

According to another exemplary embodiment of the invention, the method comprises the steps of indicating at a first receiving opening of the tube holding device an intended receipt of a sample tube with a first concentration of a target molecule, indicating at a second receiving opening of the tube holding device an intended receipt of a sample tube with a second concentration of a target molecule, and providing the first and the second receiving openings at the tube holding device at positions relative to each other, such that straight pipetting paths from a central region to an edged region of the tube holding device are facilitated from low to high target molecule concentrations.

According to another exemplary embodiment of the invention, the use of the tube holding device as defined in one of the previously defined embodiments for PCR set-up is presented.

These and other features of the invention will become apparent from and elucidated with reference to the embodiments described hereinafter.

According to another exemplary embodiment of the invention, a computer program element for PCR sample preparation and for PCR set-up which, when being executed by a processor, is adapted to carry out the steps as described herein and in the claims.

The computer program element presented herein may be part of a computer program, but it can also be an entire program by itself. For example the computer program element may be used to update an already existing computer program to get to the present invention. The computer readable medium may be seen as a storage medium, such as for example, a USB stick, a CD, a DVD, a data storage device, a hard disk, or any other medium on which a program element as described above can be stored.

BRIEF DESCRIPTION OF THE DRAWINGS

Exemplary embodiments of the invention will be described in the following drawings.

In principle, identical parts are provided with the same reference symbols in the figures.

DETAILED DESCRIPTION OF EMBODIMENTS

Figure 1:
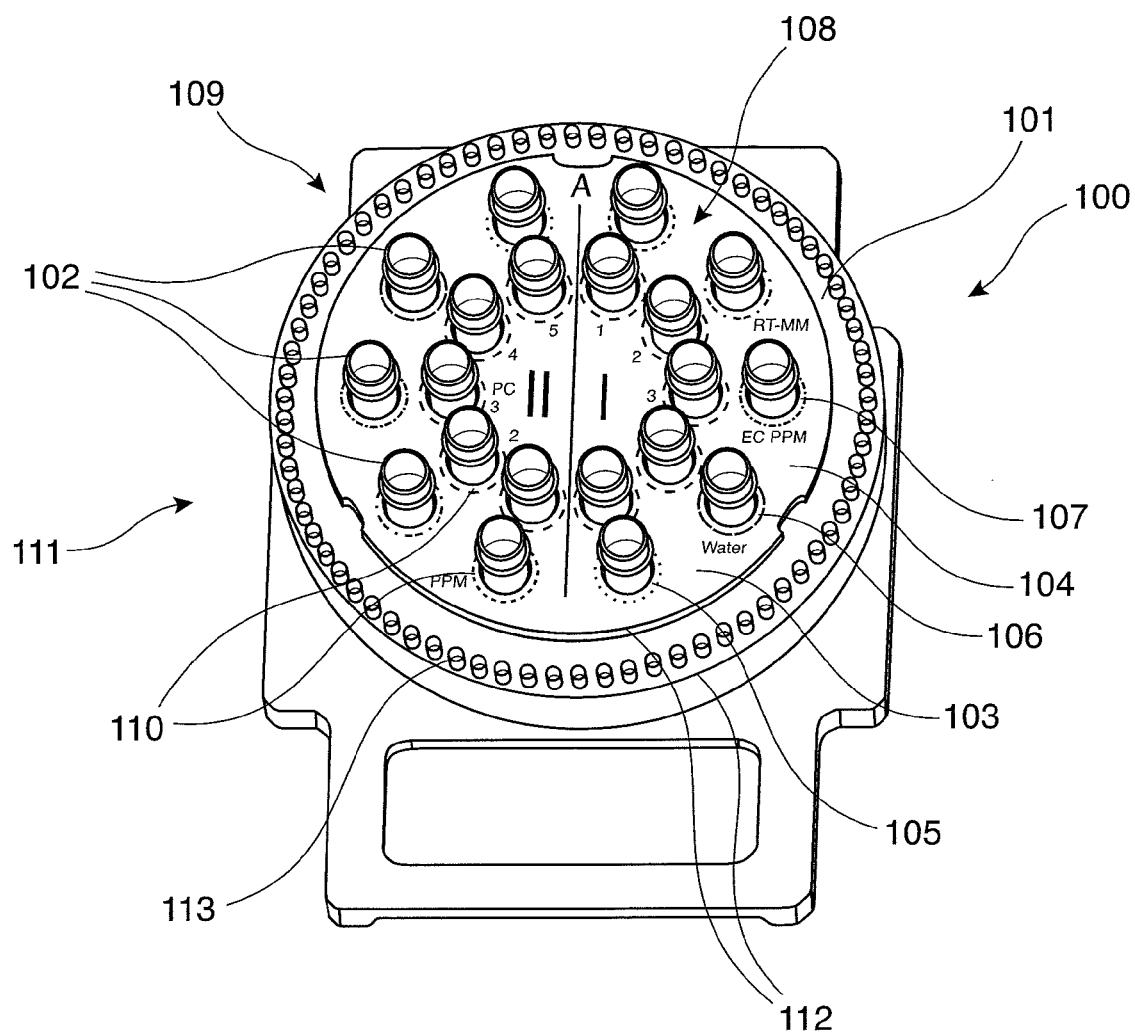
FIGS. 1 and 2 schematically show different systems for PCR sample preparation and for PCR set-up according to exemplary embodiments of the invention.

FIG. 1 schematically shows a system 100 for PCR sample preparation and for PCR set-up. The system 100 comprises a loading device 101 for receiving sample tubes 102 for setting up a PCR. The loading device comprises a first receiving section, wherein the first receiving section comprises at least a first receiving opening and a second receiving opening. In FIG. 1 the tube holding device 103 is shown in the attached position to the loading device, such that the first receiving opening and the second receiving opening of the loading device are not shown in here. However, the first and the second receiving openings are respectively adapted to receive a sample tube. As can be seen in FIG. 1, a large plurality of receiving openings 105 of the tube holding plate 104 is comprised. Each receiving opening 105 of the tube holding plate 104 is shown with a received and inserted sample tube 102. As can be gathered from the two divided parts of the tube holding plate 104, a first plurality of sample tubes for a first PCR assay 108 is depicted on the right hand side. Furthermore, a second plurality of sample tubes for a second PCR assay 109 is depicted on the left hand side of FIG. 1. All sample tubes are removeably attached to the tube holding device by means of the respective receiving opening.

Furthermore, the tuber holder plate comprises a color code 110 as an embodiment of a coding element for indicating PCR related purpose of the receiving opening of the tuber holder plate. Due to the black and white illustration of the Figures shown here, the colour can not be seen. For example, a different color per receiving opening may used. Further, a different color per receiving opening may used, but receiving openings of different assay segments 108, 109 but for the same, i.e. the corresponding sample, tube may use the same colour. Additionally or alternatively, the information may be encoded by using different types of symbols. For example, in FIG. 1 dotted lines, dashed dotted lines as well as different dashed lines with different distances between the lines are shown as exemplary embodiments of coding elements. If desired, they may be used all in one colour but also different colors, as described above, can be used. The same holds true for FIGS. 2, 4, 5, 6, 7 and 9 to 16. In this embodiment, the loading device 101 is embodied as a PCR thermorack 111. Furthermore, the shown loading device comprises a second receiving section receiving a plurality of PCR reaction chambers 113. In this embodiment, a circular provision of a plurality of PCR reaction chambers is depicted.

Furthermore, the tube holding plate 104 of FIG. 1 comprises a coding element at each receiving opening for indicating which substances are to be positioned in the respective receiving opening by means of the sample tube. As can be gathered from FIG. 1, exemplary abbreviations are marked on the tube holding plate, like "EC PPM" for extraction control primer and probe mixture, "PC" for positive control, "PPM" for primer and probe mixture, and/or "QS" for quantitative standard. However, these abbreviations are only exemplary embodiments of coding elements used at the receiving openings of the tuber holder plate. Furthermore, it can be gathered from FIG. 1 that the loading device and the tube holding device have a circular shape 112.

Figure 2:
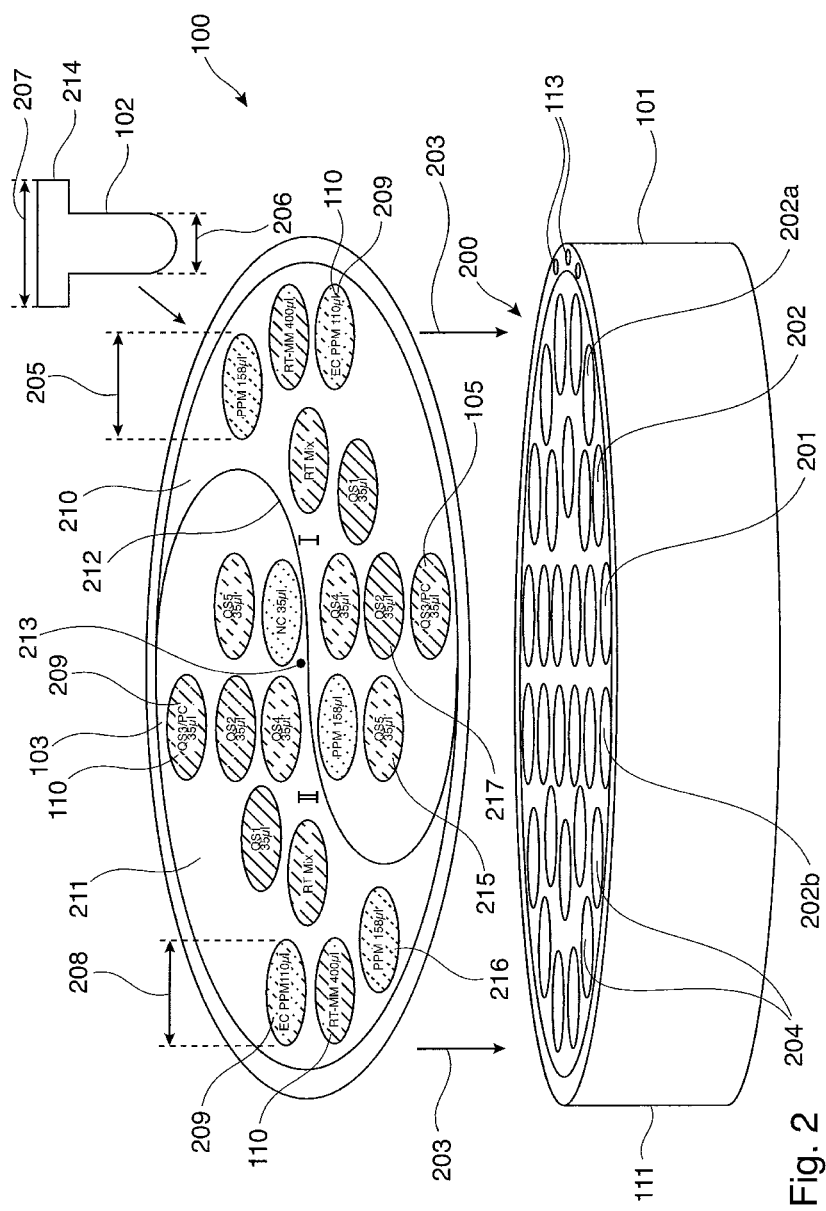

FIG. 2 shows another system 100 for PCR sample preparation and for PCR set-up according to another exemplary embodiment of the invention. The loading device 101 is shown with a plurality of receiving openings, like the first receiving opening 201 and the second receiving opening 202. Furthermore, the tube holding device 103 is also shown with a plurality of receiving openings 105. By means of a downward movement, the tube holding device is attachable to the loading device such that the receiving opening 105 of the tube holding device is aligned with at least one of the first receiving opening 201 and the second receiving opening 202 of the loading device and simultaneously covers the other of the first and the second receiving openings of the loading device. Also further exemplary embodiments of receiving openings 215 to 217 of the tube holding device are shown. Furthermore, a sample tube 102 is depicted in FIG. 2 which can be inserted into the tube holding device and simultaneously be inserted into the holding device due to the attachment of both elements. The diameter 205, 208 of the receiving openings 105 of the tube holding device is larger than the diameter 206 of the sample tube 102. Furthermore, the diameter 205, 208 of the receiving openings 105 of the tube holding device is smaller than the diameter 207 of the collar 214 of the sample tube. Therefore, an engagement between the tube holding device and the sample tube is realized due to insertion. Furthermore, a color code 110 for indicating a PCR related purpose of the receiving opening of the tube holding device 103 is shown in FIG. 2. The color code is a colored surface 209 of the tube holding device. The color codes are shown here symbolically as circular surfaces indicated by different dashed lines and dashed dotted lines. Thus, different shadings or hatchings are used. Therein, different lines represent one type of coding element, i.e. one colour. However, a circumferential ring around the respective receiving opening may be an embodiment of such a color code of the present invention. Alternatively, if desired, the receiving openings may comprise lids or elastic foils with slits such that sample tubes can be inserted. In this embodiment, the circular surfaces with different shadings represent the differently colored lids or foils.

The system 100 of FIG. 2 comprises first and second PCR assay segments 210, 211 of the tube holding device, and they are arranged relative to each other in a geometrical manner, such that first and second segments are divided by a curved line 212 passing a center 213 of the circular tube holding device. The first surface segment 210 and a second surface segment 211 respectively comprise a plurality of receiving openings. The colored surface 209 as a color code may be provided in various forms at the respective receiving opening. The loading device 101 is in the embodiment of FIG. 2 embodied as a PCR thermorack 111. In the embodiment of FIG. 2, a first receiving opening 201 will be aligned with the receiving opening 105 of the tuber holding plate 103 when they are attached together. Moreover, the second receiving opening 202 will be covered by the tube holding device. The same holds true for further receiving openings 202a and 202b which will also be covered in the attached position. In the state which is shown in FIG. 2 in which the tube holding device is not yet attached to the loading device, the first receiving section 200 can be seen. Additionally, a plurality of PCR reaction chambers 113 is shown in a circumferential region of the loading device 101.

Figure 3:
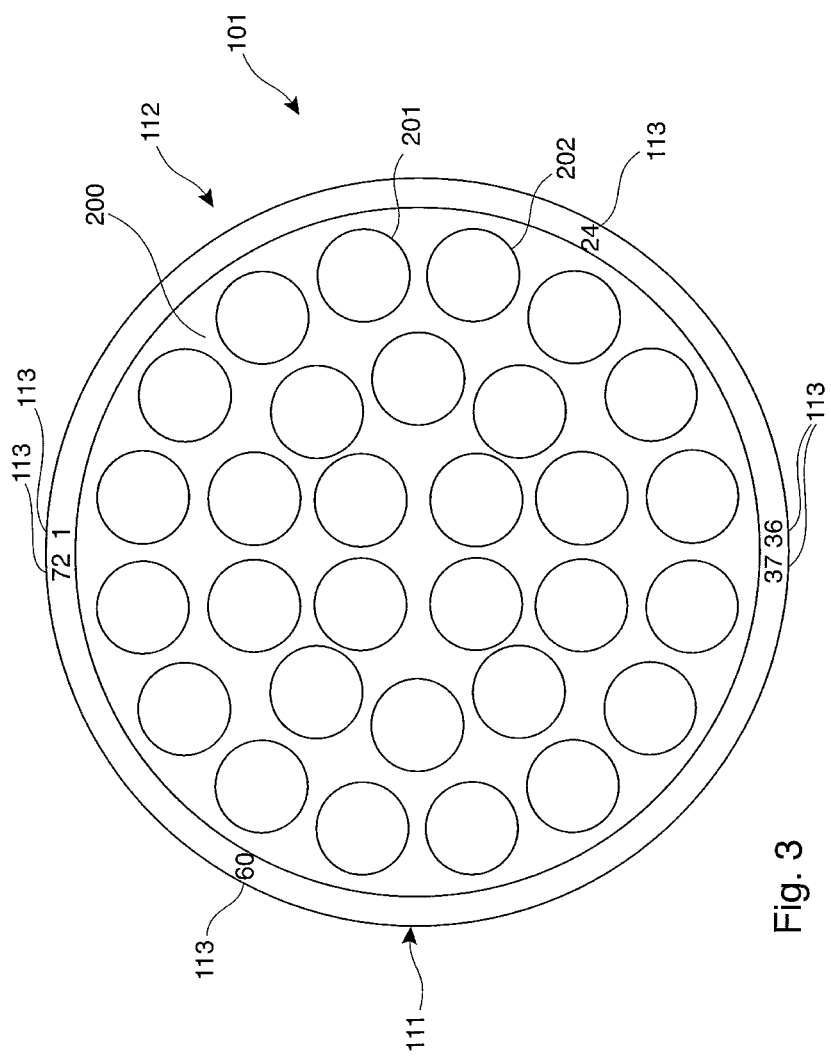
FIG. 3 schematically shows a loading device which can be used for a PCR sample preparation and for PCR set-up according to another exemplary embodiment of the invention.

FIG. 3 schematically shows a loading device 101 which can be used for PCR sample preparation and for PCR set-up in combination with several embodiments of the present invention. The loading device 101 is embodied as a thermorack for PCR purposes 111. The top view of FIG. 3 onto the loading device allows for a view into the circumferential region at which a plurality of PCR reaction chambers 113 can be positioned. The first receiving section 200 is shown in FIG. 3. The first receiving section 200 comprises the first receiving opening 201 and the second receiving opening 202. Depending on the configuration of the used assay specific tube holding device, even more of the shown 30 receiving openings of the loading device 101 may be seen as of the first type of receiving openings and of the second type of receiving openings. In principle, the first type of receiving openings is the one which is aligned with another receiving opening of the tube holding device in an attached position. The second type of the receiving openings is the one which is covered by the tube holding device. This is applicable for all herein presented embodiments. This can be gathered for example from the following FIG. 15 in which 12 receiving openings of the loading device are aligned with the corresponding receiving openings of the tube holding device. The remaining receiving openings of the loading device are covered by the tube holding device. As can be gathered from the numbering of the circumferential region, 72 PCR reaction chambers may be placed around the first receiving section 200. However, the number of 72 is only an exemplary embodiment and may be higher or lower if desired by the user. Furthermore, the 30 receiving openings of FIG. 3 of the shown loading device 101 may be configured to receive sample tubes of for example 1.5 ml and/or 0.5 ml. Further, also other sample tubes may be received by the same or differently shaped receiving openings.

Figure 4:
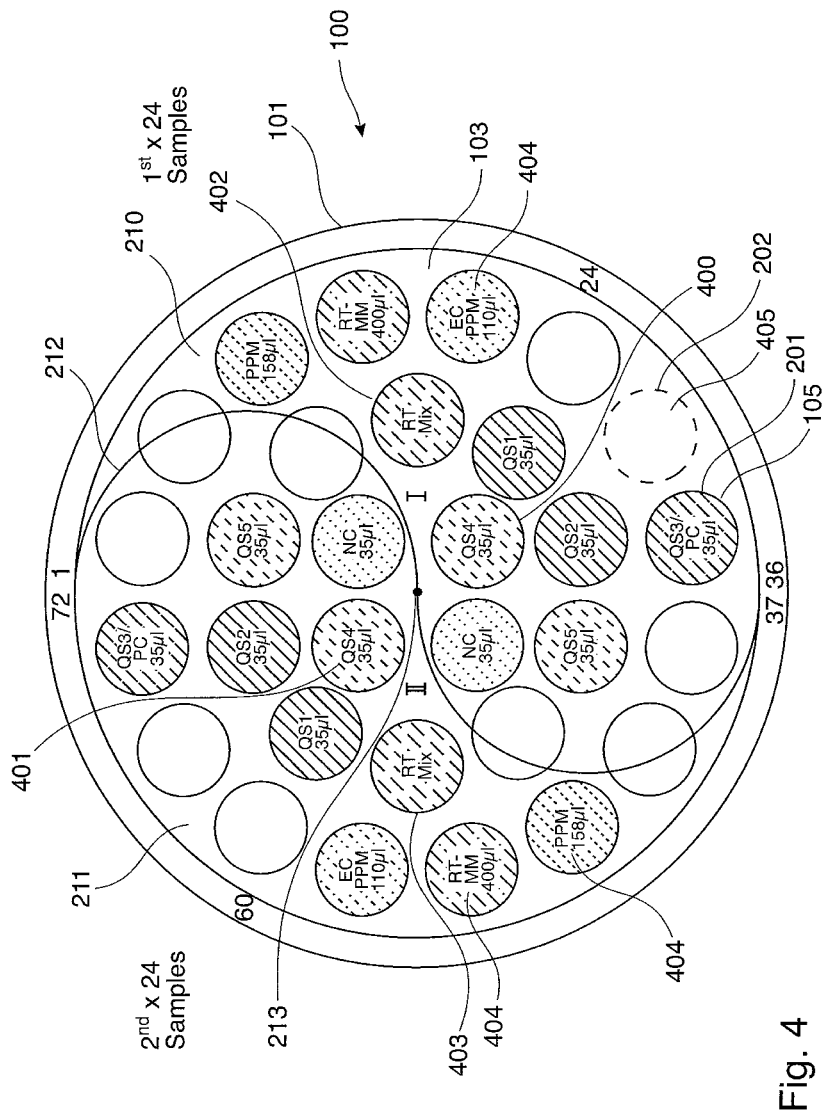
FIGS. 4 to 7 schematically show different systems for PCR sample preparation and for PCR set-up according to exemplary embodiments of the invention.

According to another exemplary embodiment of the invention, FIG. 4 shows a system 100 for PCR sample preparation and for PCR set-up with a tube holding device 103 which can be used for one assay or also for two different assays. Explanations regarding the abbreviations PC, PPM, EC PPM, QS, and others presented above apply mutatis mutandis also for FIG. 4. The loading device 101 is shown in an attached configuration with the tube holding device 103. The first surface segment 210 and the second surface segment 211 are arranged symmetrically to the central point 213 of the circular-shaped tube holding device 103. The segments are separated by the curved line 212. As can be gathered from the lower part of FIG. 4, the receiving opening 105 of the tube holding device is aligned with the first receiving opening 201 of the loading device 101. In contrast to that, the second receiving opening 202 is covered 405 by the surface of the tube holding device. The second receiving opening is only indicated by a dashed line. The feature that the tube holding device simultaneously covers the second receiving opening of the loading device is depicted with reference sign 405. Furthermore, the first surface segment 210 comprises at least one color code 400 indicating a first color of a receiving opening of the tube holding device. The second segment comprises at least one color code 401 indicating a second color of a receiving opening of the tube holding device. Furthermore, the first and the second colors are the same. Additional color codes 402 to 404 are shown in FIG. 4.

Figure 5:
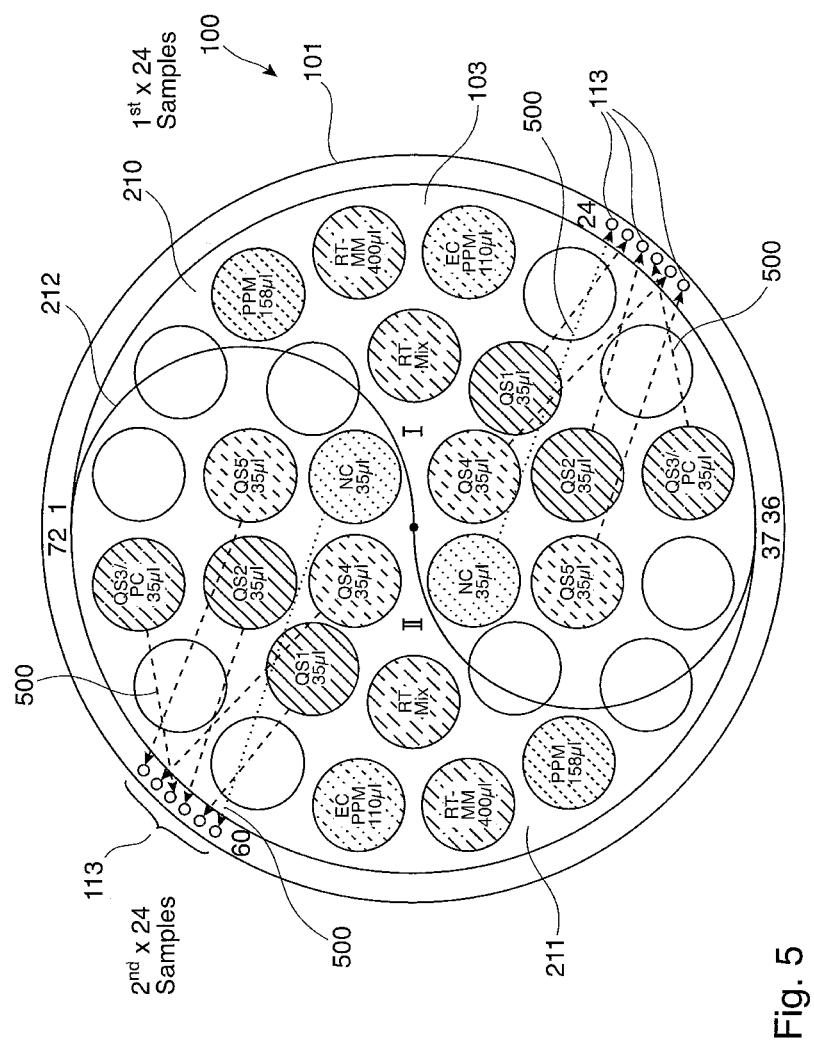

FIG. 5 depicts another exemplary embodiment of a system 100 according to another exemplary embodiment of the invention. A loading device 101 is provided with a plurality of PCR reaction chambers 113. Furthermore, the first surface segment 210 and the second surface segment 211, as already described with regard to the previously described figures, are presented. As can be gathered from FIG. 5, the tube holding device 103 comprises a plurality of receiving openings at which an intended receipt of a sample tube containing a specific concentration of a target molecule is indicated, respectively. This is indicated by the abbreviations QS1, QS2, QS3, QS4, and QS5. This abbreviation means quantitative standard. The positions of the receiving openings are configured at the shown tube holding device such that a pipetting path 500 from a central region of the tube holding device towards an edge region of the tube holding device, i.e. where the PCR chambers 113 are positioned, crosses only receiving openings, at which an intended receipt of a sample tube with a specific concentration of a target molecule is indicated, from low concentration to high concentration. This may further increase the reliability and reproducibility of the subsequently performed PCR cycle. In other words, the presented embodiment of FIG. 5 positions the receiving openings for the specifically concentrated target molecule solution sample tubes, such that direct pipetting paths 500 towards the PCR reaction chambers 113 are facilitated in such a way that when pipetting from a sample tube with a specifically concentrated target molecule, only other sample tubes with a higher concentration are crossed during the pipetting. Therefore, QS will only cross from low to high. This may minimize cross contamination during PCR set-up. This is an advantage of the present invention. In a further aspect of the present invention a system with such a tube holding device and a pipetting program performing or causing the pipetting along said pipetting paths as described herein in several embodiments is presented.

Therein, the term "from a central region towards an edge region of the tube holding device" shall be understood as describing direct pipetting paths which are direct outwards movements; thus starting at a first radial position and ending at a second radial position, wherein the first radial position is more central that the second radial position.

Figure 6:
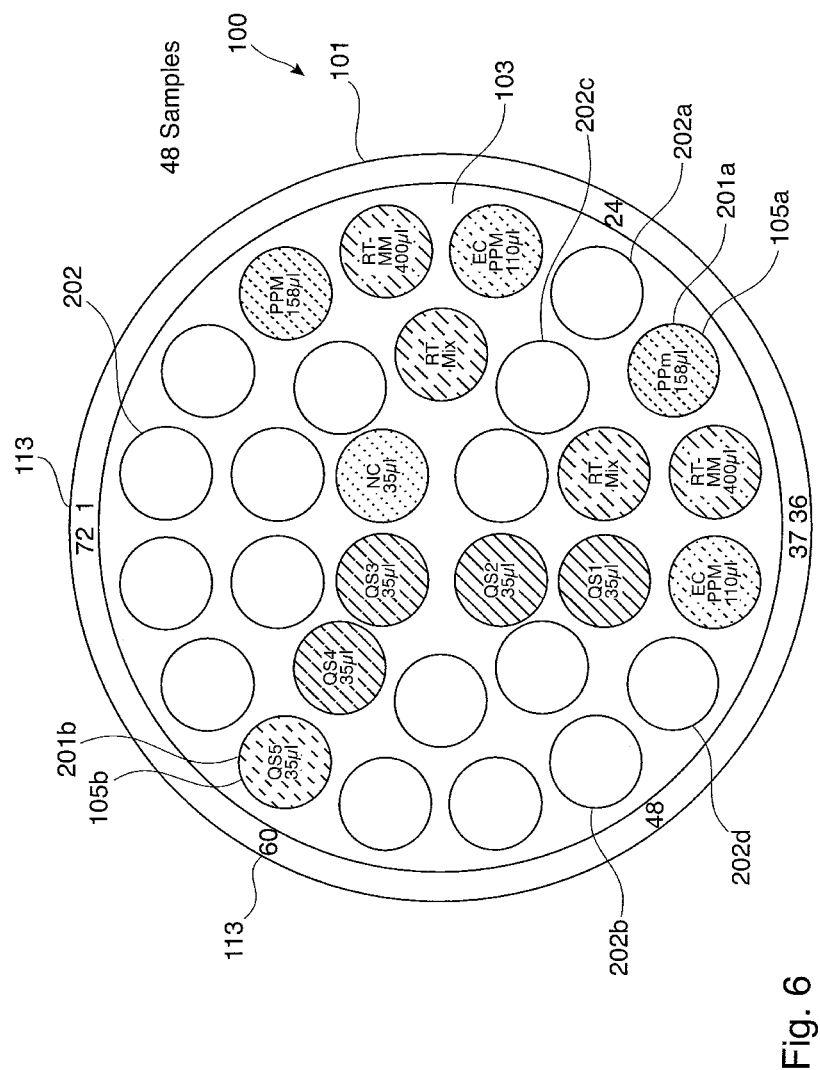

According to another exemplary embodiment of the invention, FIG. 6 also shows a system 100 comprising a loading device 101 and a tube holding device 103. A plurality of PCR reaction chambers 113 may be placed in a section which is outside of the central section. The first receiving openings 201a to 201b are shown. Furthermore, second receiving openings 202, 202a to 202d are also shown in FIG. 5. Two exemplary alignments are shown with reference signs 105a, 201a, 105b, and 201b, where two pairs of receiving openings are aligned when the tube holding device 103. The presented embodiment may, for example, be used for assays where the same assay is used in all 72 PCR reaction chambers.

Figure 7:
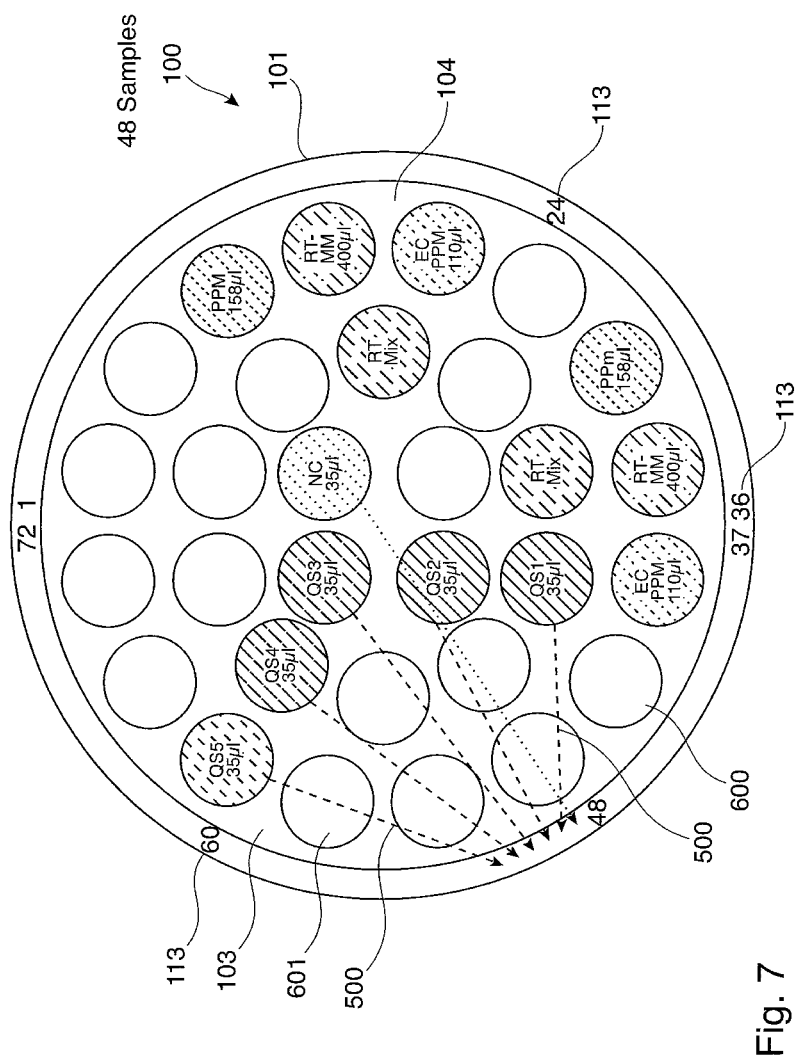

FIG. 7 schematically shows a system 100 for PCR sample preparation and PCR set-up which inter alia comprises a loading device 101 and a tuber holding plate 104. The first receiving section of the loading device 101 is centrally positioned, and the PCR reaction chambers 113 are received by the loading device at a second receiving section which is positioned exterior of the central position of the first receiving section. The shown configuration of the tube holding plate 104 facilitates pipetting along straight paths 500 from a receiving opening with a coding element for a sample tube containing a specific concentration of a target molecule into the second receiving section, which paths only cross covered receiving openings of the loading device. The receiving openings which are covered are exemplarily shown with reference 600 and 601.

Figure 8:
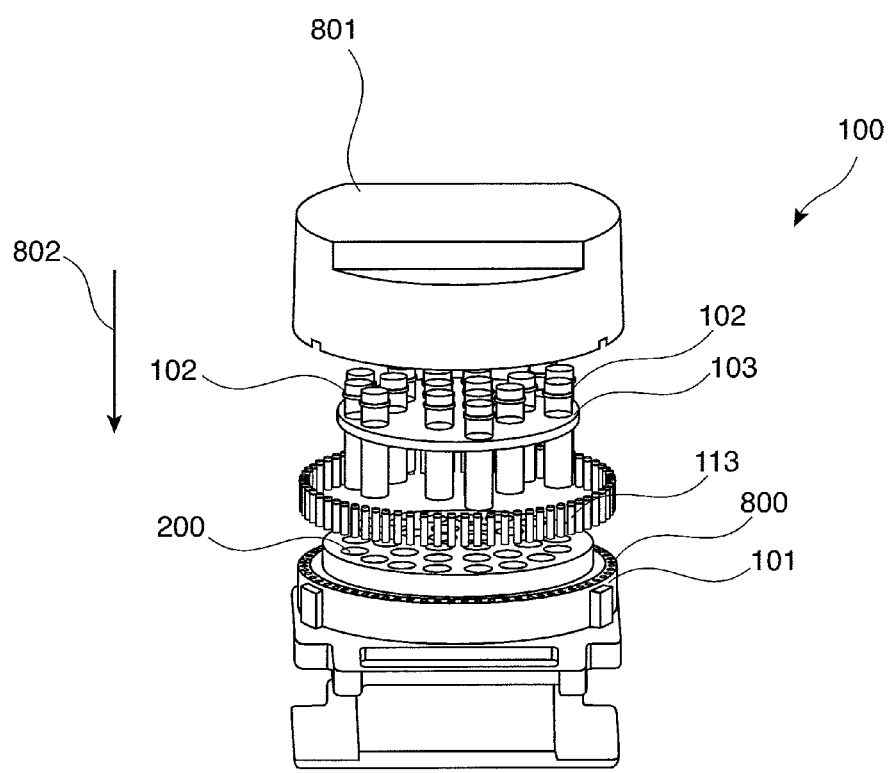
FIG. 8 schematically shows a system with a cover according to another exemplary embodiment of the invention.

FIG. 8 shows another exemplary embodiment of a system 100 which comprises a loading device 101, sample tubes 102 which are received by tube holding device 103 onto which a cover 801 can be placed simultaneously. The second receiving section 800 is configured to receive a plurality of PCR reaction chambers 113. The first receiving section 200 elongates in a circular manner and comprises a plurality of receiving sections to receive sample tubes 102. Due to a downward movement indicated by arrow 802, the attachment of the tube holding device 103 to the loading device 101 and the covering are completed. As can be gathered form FIG. 8, the cover 801 comprises recesses in it's wall which correspond to protrusions of the loading device 101. The recesses and the protrusions are configured to engage each other. this may further improve the closing or locking possibility of the device 100.

Figure 9:
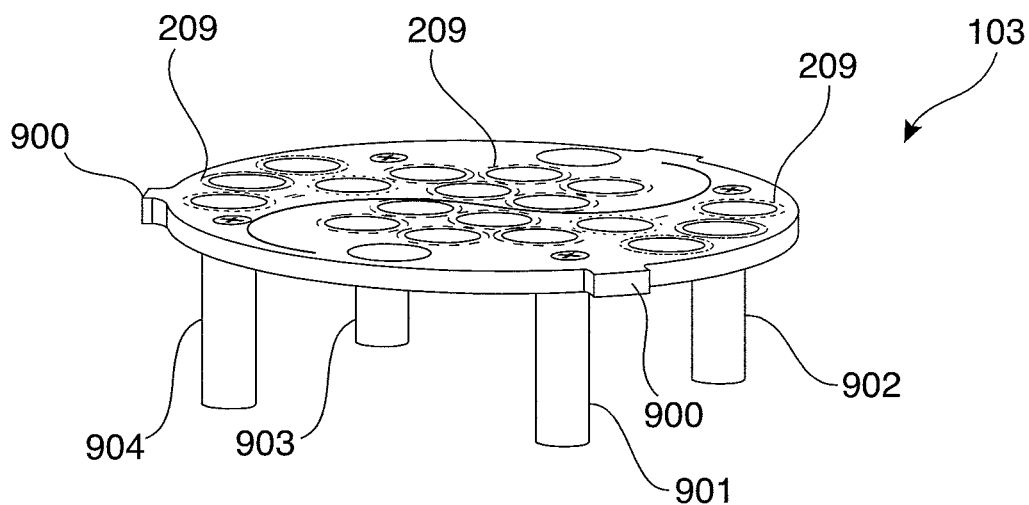
FIG. 9 schematically shows a tube holding device which can be used for PCR set-up and PCR sample preparation according to another exemplary embodiment of the invention.

FIG. 9 schematically shows a tube holding device 103 which comprises a plurality of receiving openings for a two assay based PCR set-up. A plurality of color surfaces 209 are comprised as color codes at the tube holding device 103. Furthermore, attachment means 900, here embodied as radial protrusions, are comprised in order to enable for the attachment of the device at the loading device. Moreover, stabilizing protrusion elements 901 to 904 are shown, which are configured to be inserted into a receiving opening of the loading device to stabilize the attachment of the tube holding device 103 at the loading device (not shown in FIG. 9).

Figure 10:
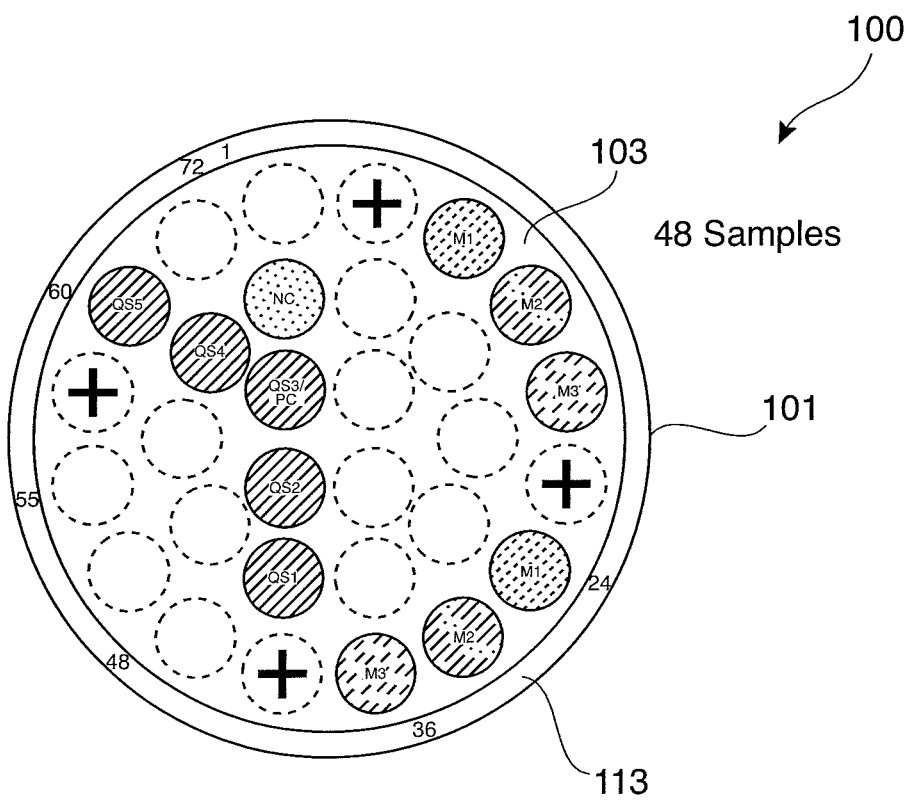
FIGS. 10 to 16 schematically show different systems for PCR sample preparation and for PCR set-up according to exemplary embodiments of the invention.

FIG. 10 shows a system 100 for PCR sample preparation and for PCR set-up according to another exemplary embodiment of the invention. A loading device 101 is depicted in FIG. 10 as well as a tube holding device 103. The plurality of PCR chambers 113 is symbolically shown by the numbers 1, 24, 36, 48, 55, 60, an 72. This embodiment of the tube holding device is configured to be used simultaneously for two assays which are the same. In particular, a coding element "M1" for a primer and probe mixture is comprised, a coding element "M2" for a master mix is comprised, a coding element "M3" for RT mix or manganese is comprised, wherein a coding element "PC" for positive control is comprised, wherein an "NC" coding element for negative control is comprised, and wherein a "QS" coding element for quantification standard is comprised by the presented tube holding device. Respective color codes may be used which are different for "M1", "M2", "M3", "PC", "NC", and "QS". However, different quantification standard receiving openings for receiving different concentrations of target molecules may be indicated with the same color but with different additional opening specific abbreviations. In other words, the presented embodiment may be provided with five "QS" receiving openings in which the sample tubes with a specific concentration of target molecules are to be inserted, wherein said openings are all coded with a color code as coding element having or indicating the same color.

Figure 11:
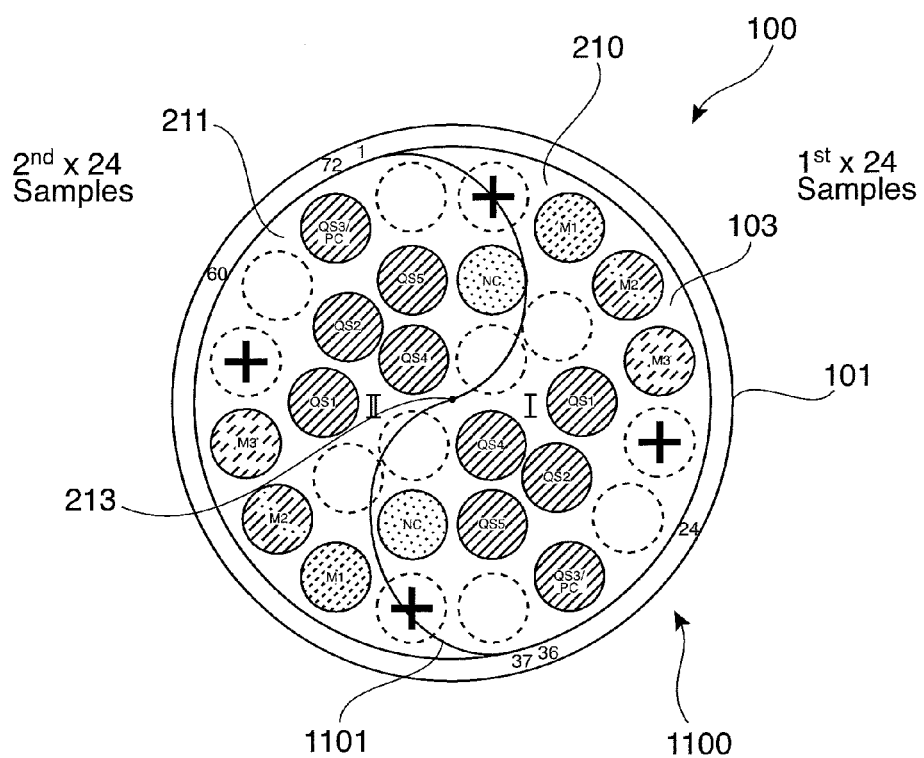

FIG. 11 shows another system 100 comprising a tube holding device for one assay or also for two different assays. As can be seen from FIG. 11, tube holding device 103 provides for a spatial distribution of its receiving openings which is point-symmetric to the central point 113. Further, first surface segment 210 and second surface segment 211, which indicate the respective space for the two different assays, are shown in FIG. 1. The curved and S-form shaped line 1101 divides the two segments. The point symmetry 1100 can easily be gathered from the top view of FIG. 11. Furthermore, the abbreviations M1, M2, M3, PC, NC, and QS are similarly used as for the previously described FIG. 10.

Figure 12:
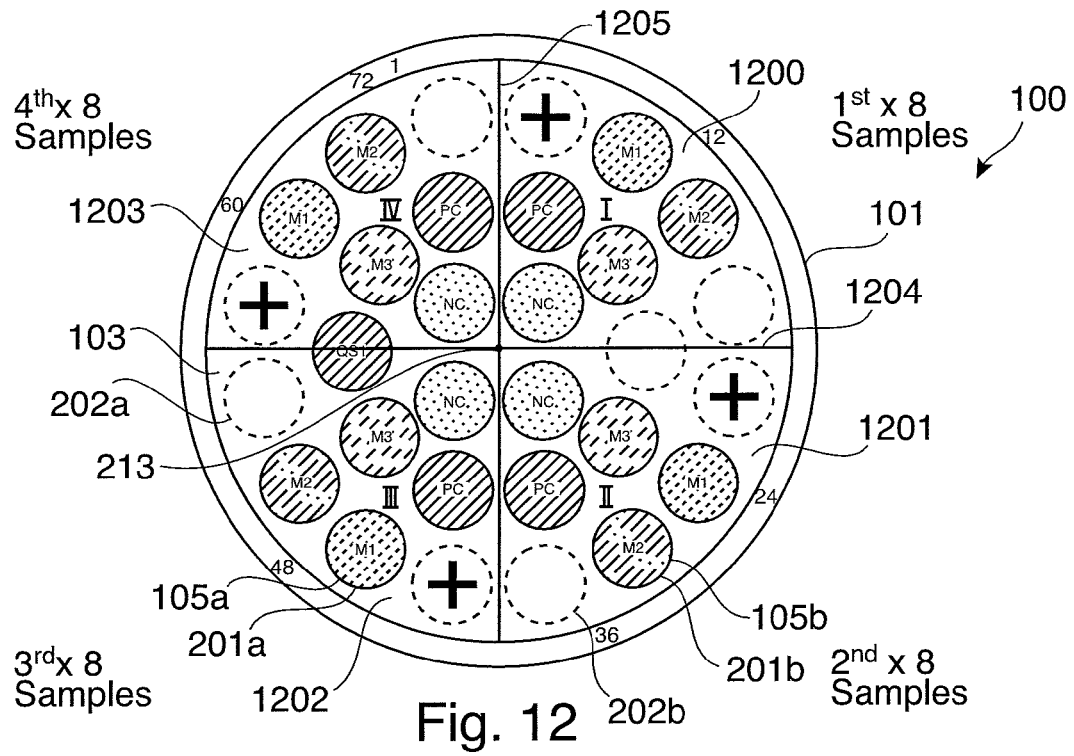

FIG. 12 describes another system 100 for PCR sample preparation and for PCR set-up comprising a loading device for receiving sample tubes and a tube holding device 103 for being attached to the loading device. In this top view of FIG. 12, the alignment of receiving openings 105a and 105b of tube holding device 103 with the corresponding receiving openings 201a and 201b of the loading device is shown. Furthermore, it can be seen that the covered second receiving openings 202a and 202b are shown as allusions, as they are covered by the plane of the tube holding device. Such allusions are also shown in FIG. 4, FIG. 5, FIG. 6, FIG. 7, FIG. 10, and FIG. 11, however, it is clearly described herein that such allusions are only indicated for clarity reasons. In any case, such receiving openings of the loading device are spatially covered by the tube holding device. The center 213 of the circular-shaped device is crossed by two straight lines 1204 and 1205, such that a four segment configuration is generated on the tube holding device 103. Thus, four segments of a circle with respective reference signs 1200 to 1203 are shown in FIG. 12. This configuration may be used for one assay or also for two different assays.

Figure 13:
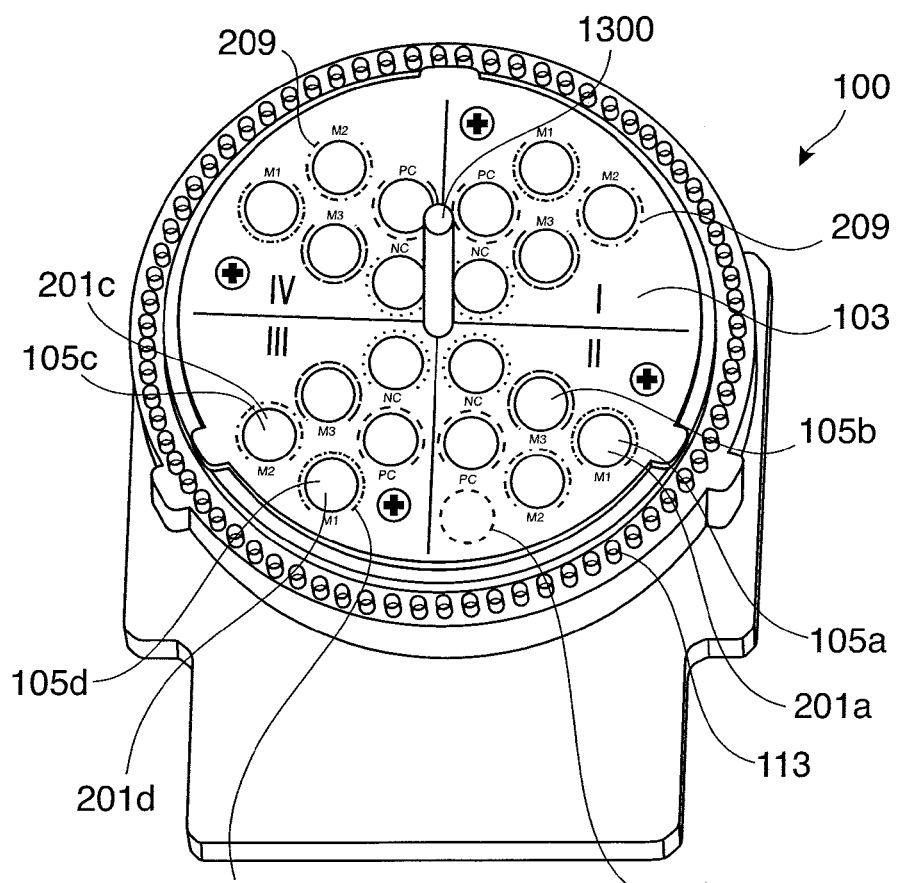

FIG. 13 shows another exemplary embodiment of a system 100, comprising a loading device 101 and tube holding device 103. As an allusion covered second receiving opening 202 of the loading device is depicted with dashed lines. Furthermore, reference signs 105a to 105b are used for the receiving openings of the tube holding device 103, which are aligned with respective receiving openings 201a to 201b of the loading device. In this four segment arrangement, colored surfaces 209 are the receiving openings are used as color codes to direct the movement of the sample tubes into the correct receiving opening. The different colours are indicated here by means of different signs, namely different dashed lines and dashed dotted lines. A plurality of PCR chambers 113 is arranged around the central part of the device, such that a direct pipetting from the center region towards the circumferential region, namely into the PCR chambers, is possible and facilitated by the presented device. Furthermore, a handle 1300 for being grasped by the user or a device is shown. The handle facilitates inserting and/or removing the tube holding device 103 into and/or from the loading device. Therefore, a fully automated and fast change of different assay specific tube holding devices is presented.

Figure 14:
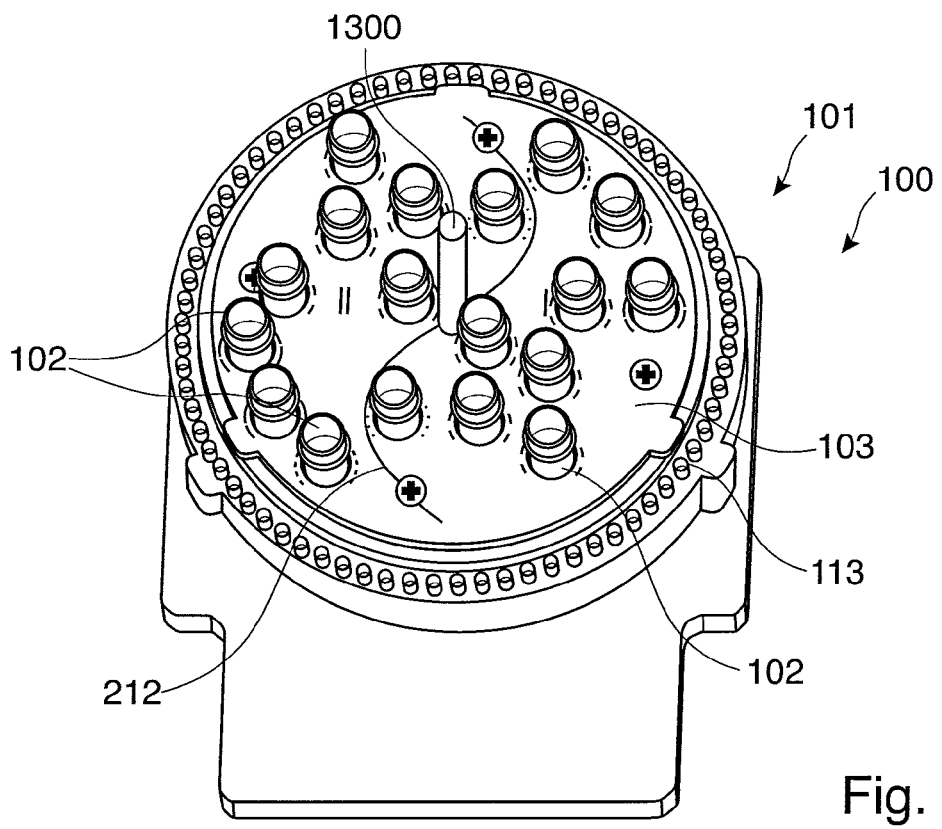

FIG. 14 shows the embodiment of FIG. 11 in a perspective view after sample tubes 102 have been inserted into the system 100. Furthermore, the handle 1300 is shown in FIG. 14, too. Regarding the remaining features and reference signs, it is kindly referred to the other Figures, particularly to FIG. 11.

Figure 15:
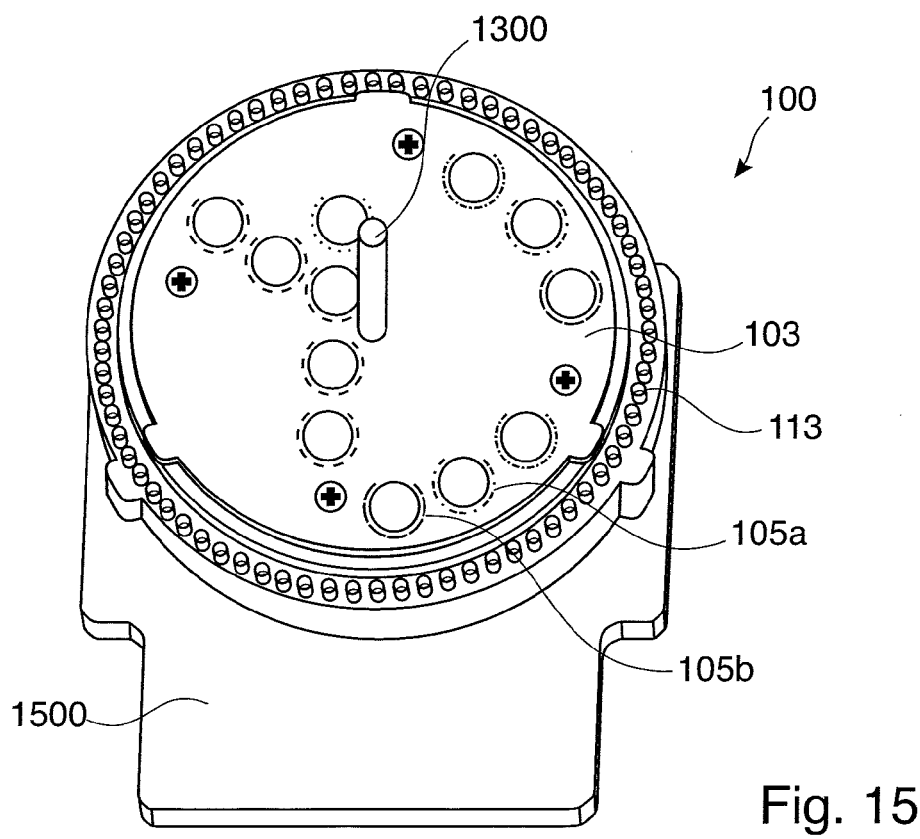

According to another exemplary embodiment of the invention, FIG. 15 shows a device 100 with a handle 1300 for being grasped by a user or an automated device. The tube holding device 103 is integrated into the loading device. An alignment of the receiving openings of the loading device is achieved for 12 receiving openings of the tube holding device, out of which 105a and 105b are marked with reference signs. Element 1500 may be seen as base plate for the loading device.

Figure 16:
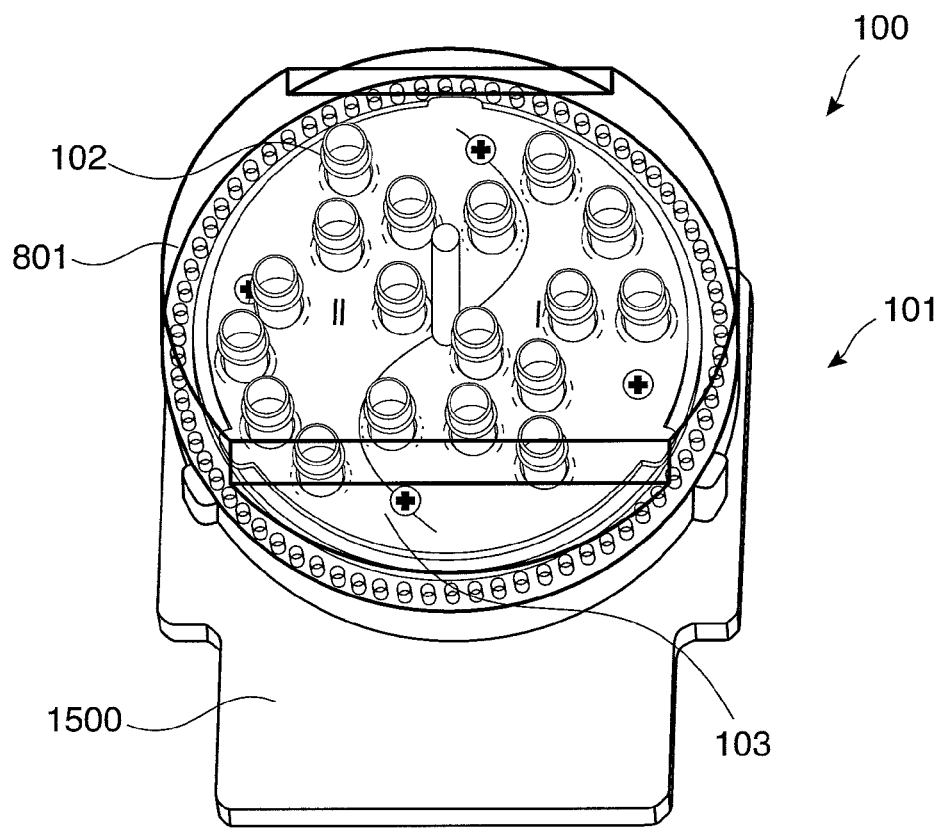

According to another exemplary embodiment of the invention, FIG. 16 shows a system for PCR sample preparation and for PCR set-up 100 which comprises the loading device 101, which is covered by transparent cover 801. Therefore, a simultaneous covering of the loading device 101 and the tube holding device 103 and the inserted sample tubes 102 is achieved. Well in line with FIG. 15, element 1500 is shown also for the embodiment of FIG. 16.

Figure 17:
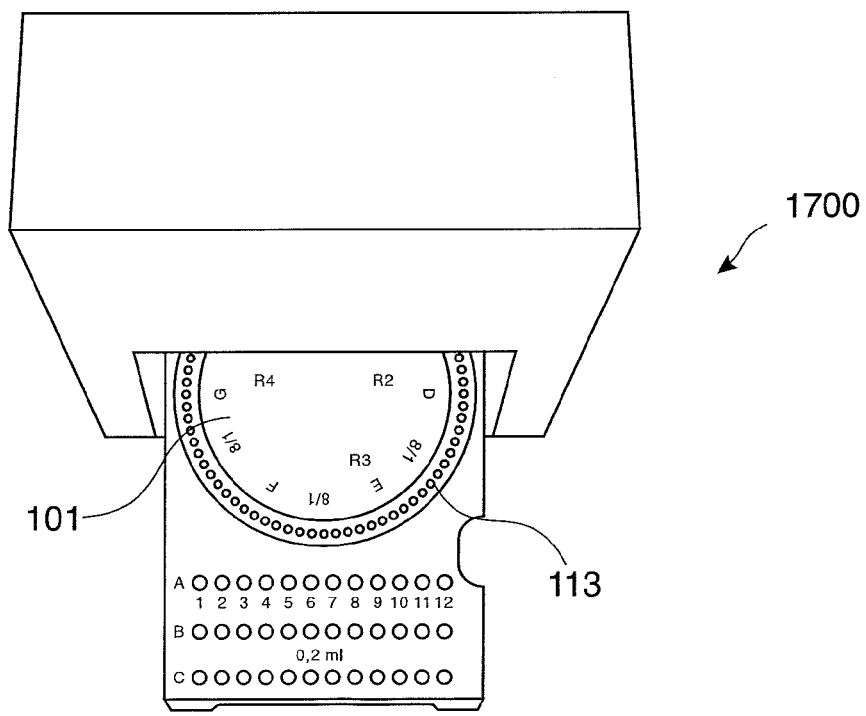
FIG. 17 schematically shows a sealing device which can be used in combination with the present invention.

FIG. 17 shows the insertion process of a plurality of PCR reaction chambers 113 which have been filled previously by means of the system of the present invention. A heat sealing apparatus 1700 is shown in order to provide for a sealing, like for example the provision of a plastic foil onto said chambers. The loading device 101 is inserted into device 1700 while carrying a plurality of PCR reaction chambers. In other words, the loading device is adapted to be receivable by a thermal sealing device.

Figure 18:
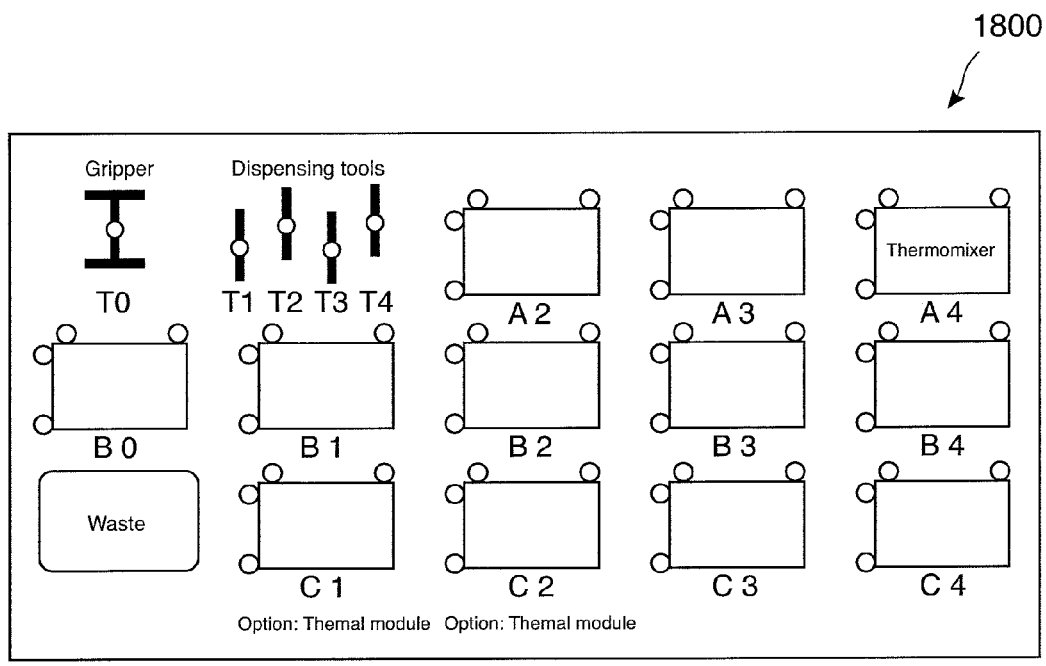
FIG. 18 schematically shows a sketch of a known automated system for PCR sample preparation only.

FIG. 18 shows a lab ware, as it is known in the art. Device 1800 provides for 11 positions for lab ware, A2, A3, B0-B4 and C1-C4.

Figure 19:
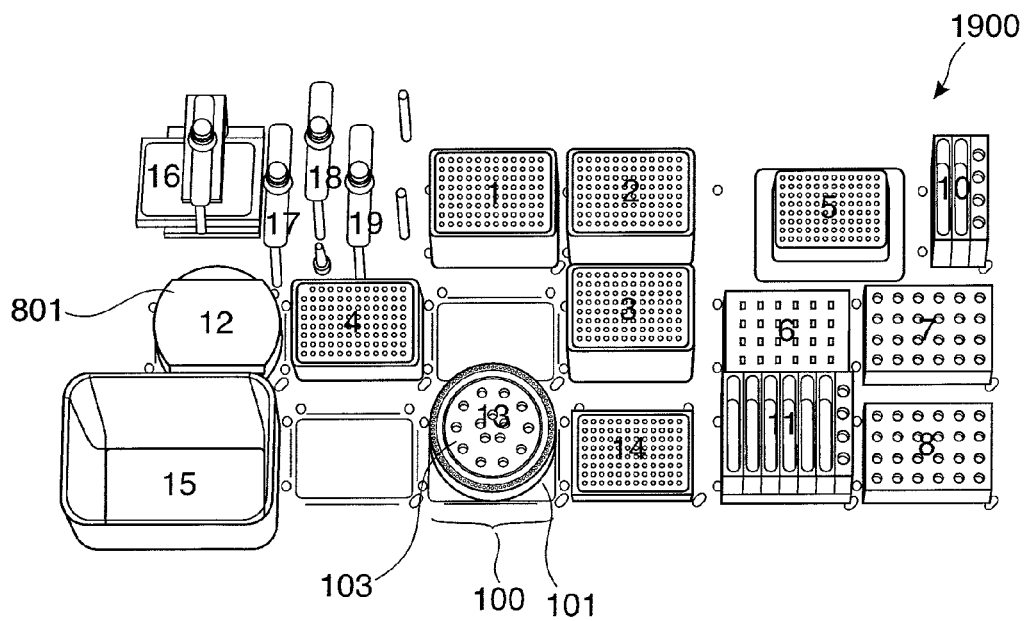
FIGS. 19 and 20 schematically show different systems for PCR sample preparation and for PCR set-up according to exemplary embodiments of the invention.

FIG. 19 provides for a fully automated sample preparation and PCR set-up device 1900 according to another exemplary embodiment of the present invention. Device 199 comprises a system 100 as has been described before with respect to FIGS. 1 to 17 and will be described hereinafter in more detail. The two components, the loading device 101 and the tube holding device 103 are depicted in FIG. 19. In addition, cover 801 is shown on the left hand side of FIG. 19. In total, the device 1900 provides for 12 positions used for lab wares. The device 100 facilitates PCR sample preparation and PCR set-up, which provides for an accelerated PCR which a user intends to do. The device 1900 is able to recognize and set-up the PCR reaction on the device 100 by automatically moving all necessary sample tubes and liquids from the remaining areas of the device 1900 for example via pipetting or via transporting sample tubes into device 100. Moreover, the device 1900 is able to automatically transport and transfer the cover 801 to the position of system 100, such that the system is covered. This may prevent potential cross carry over during the PCR sample preparation process. This is a further advantage of the present invention. The pipetting paths 500 described herein may be carried out by the system 1900. A corresponding computer program element is presented. It should explicitly be noted that this embodiment of FIG. 19 can be combined with any other embodiment of the invention disclosed herein.

Figure 20:
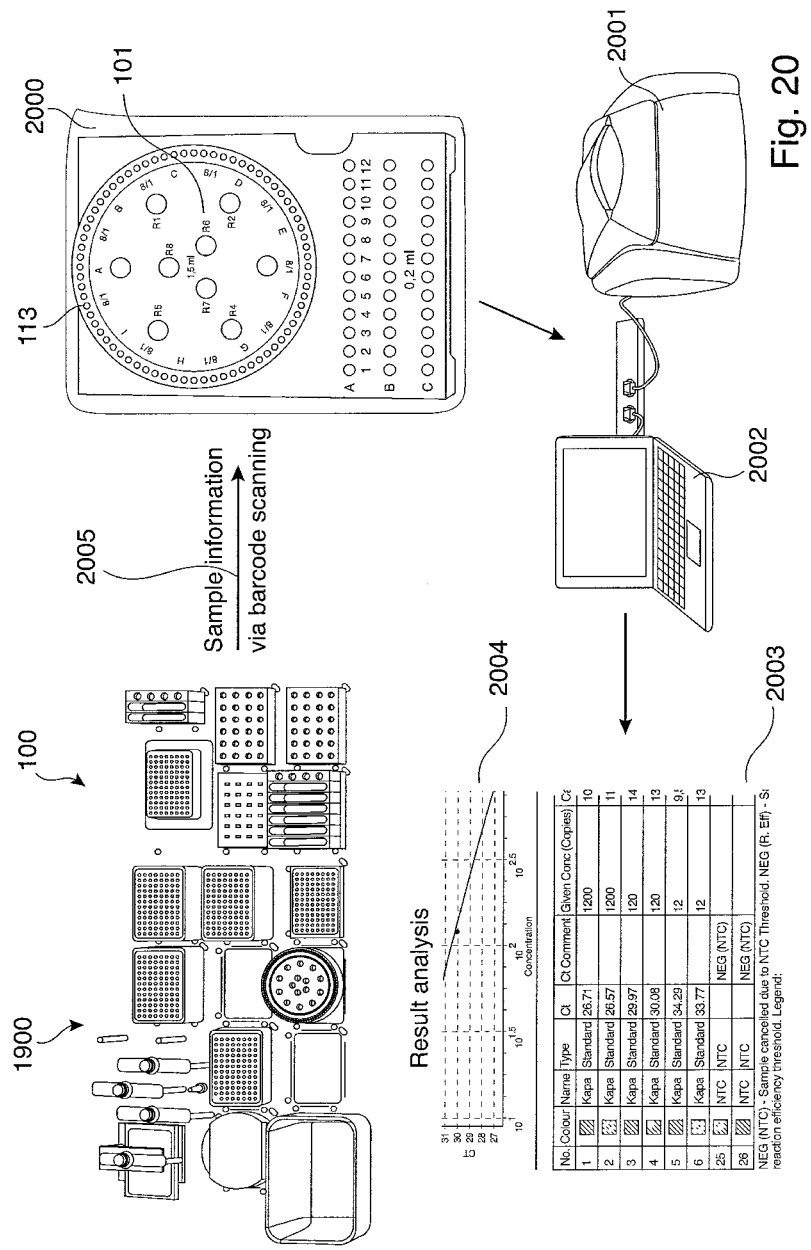

According to another exemplary embodiment of the invention, FIG. 20 shows the device 1900 which has been described in detail with respect to previous FIG. 19. Therein, the system 100 is comprised. By a process of for example barcode scanning 2500, sample information can be transferred to the calculating unit 2200 and/or the thermocycler 2100, shown in FIG. 20. It is also indicated in FIG. 20 that after the PCR sample preparation and PCR set-up in the device 1900 via system 100, a sealing foil 2000 may be provided onto the PCR chambers 113. As can be gathered from FIG. 20, loading device 101 is completely sealed together with the PCR chambers 113 by a foil 2000. The presented system of FIG. 20 provides for software which is able to recognize and set-up the PCR reaction on the loading device 101 of system 100. A subsequent PCR may be initiated automatically, based on the received sample information. For the barcode scanning, a scanner may be provided, which is not shown in FIG. 20. For data analysis, table 2300 is shown in which detailed results of the analysis are shown. Furthermore, integrated FIG. 2004 allows for graphically illustrating the obtained results of the previously described process. Therefore, the device 900 provides for interfacing data between the PCR sample preparation and PCR set-up device one the one hand and the thermocycler on the other hand is also presented by the present invention.

Figure 21:
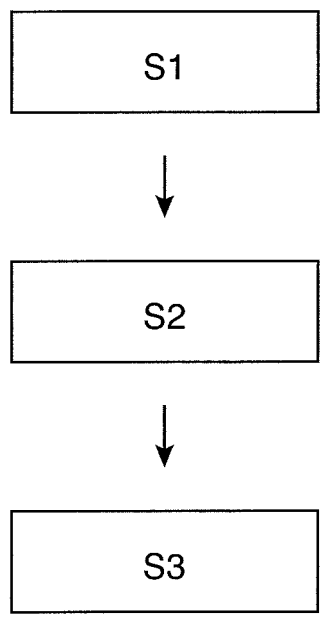
FIGS. 21 to 24 schematically show flow diagrams of different methods of different exemplary embodiments of the invention.

FIG. 21 schematically shows a flow diagram of a method of preparing a PCR. The method comprises providing for a loading device, which loading device is for receiving sample tubes for setting up a PCR. This step is shown with S1. Step S2 describes providing for a tube holding device. Therein, the loading device comprises a first receiving section which comprises at least a first and a second receiving opening. The first receiving opening and the second receiving opening are adapted to respectively receive a sample tube. The method further comprises the step attaching the tube holding device to the loading device, which is indicated with S3.

Figure 22:
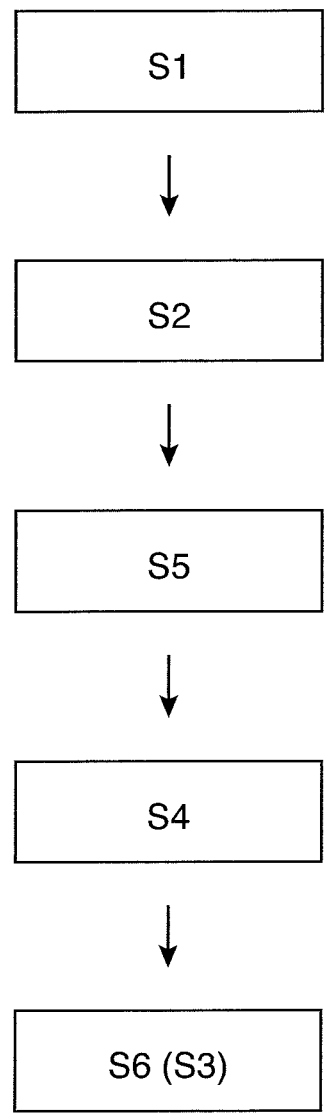

The exemplary embodiment of FIG. 22 is based on the embodiment of FIG. 21, whereas additional method steps are comprised. In particular, a sample tube is removeably attached to the tube holding device in step S5. Further, aligning the receiving opening of the tube holding device with one of the first receiving opening and the second receiving opening of the loading device, thereby simultaneously covering the other of the first and the second receiving openings is shown by step S4. Further, the sample tube is inserted into receiving opening of the loading device by attaching the tube holding device to the loading device in step S6. Consequently, S3 is inherently performed by step S6. Therefore, step S3 is indicated in brackets in FIG. 22.

Figure 23:
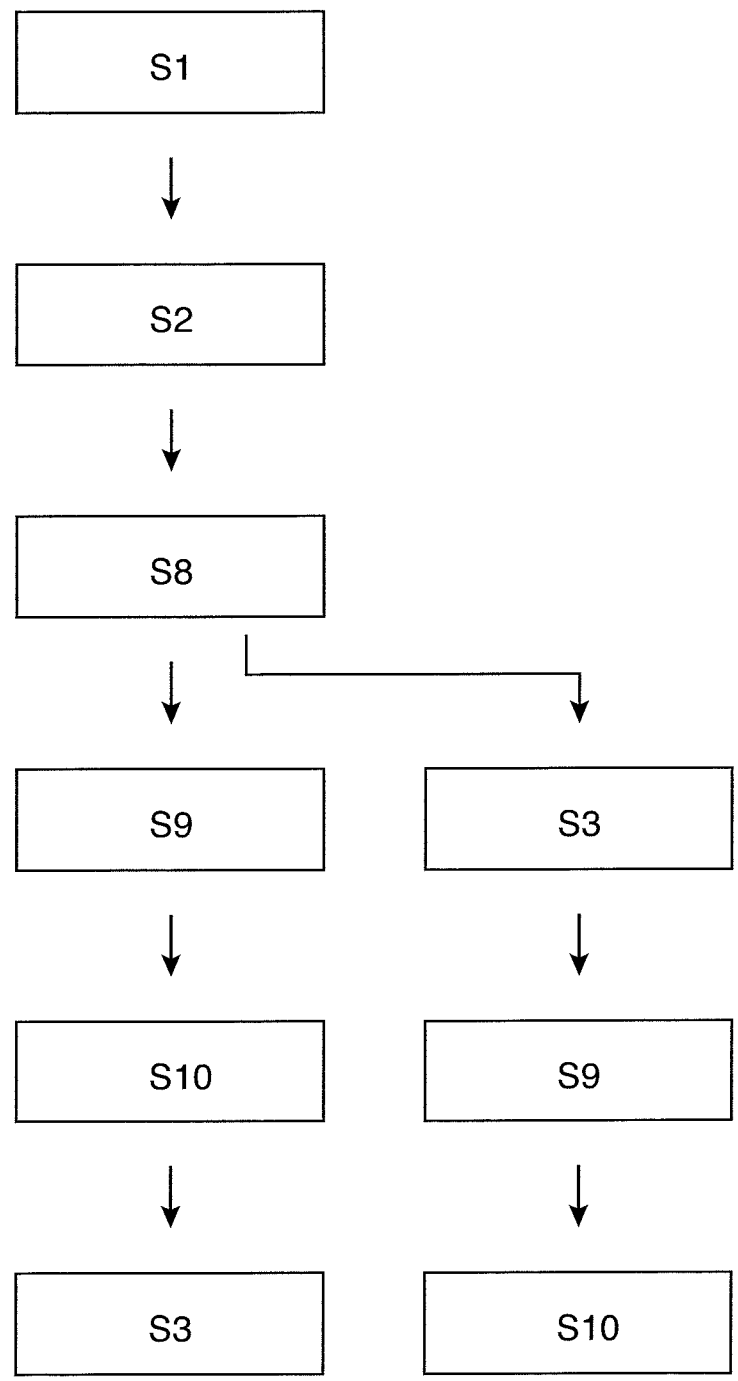

FIG. 23 shows two different flow diagrams of two different exemplary embodiments of the present invention. On the left hand side, steps S1 and S2 are performed in a similar manner as previously described with respect to FIGS. 21 and 22. In both embodiments of FIG. 23, the tube holding device comprises at least a first opening having a color code indicating a first color, and a second opening having a color code indicating a second color. Furthermore, for both embodiments of FIG. 23, a sample tube is provided with a color code indicating a third color in step S8. The first embodiment of FIG. 23, depicted on the left hand side of FIG. 23, subsequently selects the receiving opening of the tube holding device which has the same color as the color code of the sample tube in step S9. Furthermore, the sample tube is inserted into the selected receiving opening of the tube holding device in step S10. After step S10, the tube holding device is attached to the loading device in step S3. However, the second embodiment of FIG. 23, depicted on the right hand side, provides for another sequence of method steps, as will be explained hereinafter. Firstly, the attachment of the tube holding device to the loading device is generated in step S3, after which the step of selecting the receiving opening of the tube holding device which has the same color as the color code of the sample tube is performed with step S9. Finally, the sample tube is inserted into the selected receiving opening of the tube holding device in step S10, by inserting the sample tube into the attached arrangement.

Figure 24:
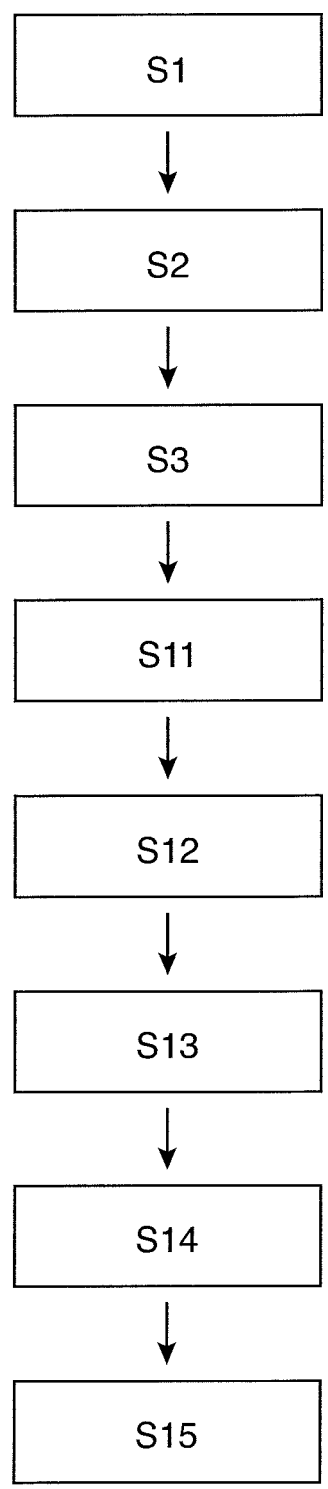

According to another exemplary embodiment of the invention, FIG. 24 describes a flow diagram of a method of preparing a PCR with several method steps. With respect to the steps S1 to S3, it is kindly referred to the explanations regarding FIGS. 21 to 23. The embodiment of FIG. 24 further provides for scanning data of at least one element, chosen from the group comprising elution plate, extraction reagents, assay reagents, sample tubes, and any combination thereof in step S11. Furthermore, the scanned data is transmitted to a calculating unit, for example calculating unit 220 of FIG. 20, for PCR purposes in step S12. Said calculating unit generates sample information in a thermocycler readable data format in step S13. In other words, the device and method of the present invention facilitates the provision of thermocycler readable data about the PCR set-up. The sample information in the thermocycler readable data format is transmitted to the thermocycler in step S14. The step of performing a PCR in a received PCR reaction chamber by the thermocycler, based on the sample information received in the thermocycler readable data format is shown with step S15 in FIG. 24.

Other variations to the disclosed embodiments can be understood and effected by those skilled in the art in practising the claimed invention, from the study of the drawings, the disclosure, and the appended claims. In the claims the word "comprising" does not exclude other elements or steps and the indefinite article "a" or "an" does not exclude a plurality. A single processor or other unit may fulfil the functions of several items or steps recited in the claims. The mere fact that certain measures are recited in mutually different dependent claims does not indicate that a combination of these measures cannot be used to advantage. A computer program may be stored/distributed on a suitable medium such as an optical storage medium or a solid-state medium supplied together with or as part of other hardware, but may also be distributed in other forms, such as via the Internet or other wired or wireless telecommunication systems. Any reference signs in the claims should not be construed as limiting the scope of the claims.

The invention claimed is:

1. A method of setting up a polymerase chain reaction ("PCR"), comprising:
    providing a loading device of an automated system for PCR configured to receive sample tubes for PCR reagents for setting up a PCR, wherein the loading device comprises a first receiving section and a second receiving section, the first receiving section comprising at least first and second receiving openings, wherein the first and second receiving openings are configured to respectively receive a sample tube; the second receiving section adapted to receive a plurality of PCR reaction chambers for PCR arranged circumferentially around the first receiving section;
    providing a tube holding device comprising a coding element for indicating which substance is to be positioned in the at least first receiving opening by means of a sample tube with a corresponding coding element, wherein the tube holding device comprises at least a first receiving opening;
    attaching the tube holding device to the loading device; and
    aligning the at least first receiving opening of the tube holding device with one of the first and second receiving openings of the loading device and simultaneously covering the other of the first and the second receiving openings of the loading device;

wherein upon said aligning and simultaneous covering, said automated system for PCR is set up.

2. The method according to claim 1, the method further comprising simultaneously removing a first plurality of sample tubes for a first PCR assay and a second plurality of sample tubes for a second PCR assay from the loading device by grasping the tube holding device and removing the tube holding device from the loading device.

3. The method according to claim 1, further comprising covering unused receiving openings of the loading device by the tube holding device.

4. The method according to claim 1, wherein the first receiving opening of the tube holding device includes a color code indicating a first color and a;
second receiving opening of the tube holding device has a color code indicating a second color,
the method further comprising:
providing a sample tube with a color code indicating a third color;
selecting the receiving opening of the tube holding device which has a same color as the color code of the sample tube; and
inserting the sample tube into the selected opening of the tube holding device.

5. The method according to claim 1, further comprising:
scanning data of at least one element chosen from a group comprising elution plate, extraction reagents, assay reagents, sample tubes, and any combination thereof; and
transmitting the scanned data to a calculating unit for PCR purposes.

6. The method according to claim 5, further comprising:
generating sample information in a thermocycler readable data format by the calculating unit;
transmitting the sample information to a thermocycler; and
performing a PCR in a PCR reaction chamber by the thermocycler based on the sample information received in the thermocycler readable data format.

7. The method according to claim 1, wherein the first receiving section is centrally positioned, and the method further comprises:
receiving PCR reaction chambers by the loading device at the second receiving section positioned exterior of the central position of the first receiving section; and
pipetting along a straight path from the first receiving opening with the coding element for indicating which substance is to be positioned in the at least first receiving opening by means of a sample tube with a corresponding coding element for a sample tube containing a specific concentration of a target molecule into the second receiving section, which path crosses covered receiving openings of the loading device only.

8. The method according to claim 1, the method further comprising:
indicating at a plurality of the receiving openings of the tube holding device an intended receipt of a sample tube containing a specific concentration of a target molecule, respectively; and
pipetting along a path between a central region of the tube holding device and an edge region of the tube holding device thereby crossing receiving openings, at which an intended receipt of a sample tube with a specific concentration of a target molecule is indicated, from low concentration to high concentration.

9. The method according to claim 1, comprising:
indicating at the first receiving opening of the tube holding device an intended receipt of a sample tube with a first concentration of a target molecule;
indicating at a second receiving opening of the tube holding device an intended receipt of a sample tube with a second concentration of a target molecule; and
providing the first and second receiving openings at the tube holding device at positions relative to each other such that straight pipetting paths from a central region to an edged region of the tube holding device are facilitated from low to high target molecule concentrations.

10. A fully automated system for a polymerase chain reaction ("PCR") sample preparation and for PCR set-up and for carrying out a complete PCR, the system comprising:
a thermocycler;
a calculating unit configured to generate sample information in a thermocycler readable data format, wherein the thermocycler and the calculating unit are in communication with each other;
a loading device for receiving sample tubes for setting up a PCR, wherein the loading device comprises a first receiving section and a second receiving section, the first receiving section comprising at least first and second receiving openings, and the first and second receiving openings being adapted to respectively receive a sample tube, the second receiving section adapted to receive a plurality of PCR reaction chambers for PCR arranged circumferentially around the first receiving section; and
a tube holding device attached to the loading device, the tube holding device comprising a coding element for indicating which substance is to be positioned in the at least first receiving opening by means of a sample tube with a corresponding coding element, wherein the tube holding device comprises an at least a first receiving opening, wherein the tube holding device is attachable to the loading device such that the at least first receiving opening of the tube holding device is aligned with at least one of the first and second receiving openings of the loading device and simultaneously covers the other of the first and the second receiving openings of the loading device,
wherein the thermocycler is configured to automatically perform a PCR in a received PCR reaction chamber based on the sample information received in the thermocycler readable data format.

11. The system according to claim 10, wherein the tube holding device comprises a coding element at the at least first receiving opening for indicating which substance is to be positioned in the at least first receiving opening by means of the sample tube.

12. The system according to claim 10, wherein the tube holding device is configured to be assay specific with respect to a geometrical distribution of the at least first receiving opening.

13. The system according to claim 10,
wherein the first receiving section is centrally positioned,
wherein the loading device is adapted to receive the PCR reaction chambers at the second receiving section positioned exterior of the central position of the first receiving section, and
wherein the tube holding device is configured for a specific assay with respect to the geometrical distribution of the receiving openings such that straight pipetting paths from a receiving opening with a coding element for a sample tube containing a specific concentration of a target molecule into the second receiving section are facilitated, which paths cross covered receiving openings of the loading device only.

14. The system according to claim 10,
wherein the tube holding device comprises a plurality of receiving openings at which an intended receipt of a sample tube containing a specific concentration of a target molecule is indicated, respectively, and
wherein the positions of the receiving openings is configured such that a path between a central region of the tube holding device and an edge region of the tube holding device crosses receiving openings, at which an intended receipt of a sample tube with a specific concentration of a target molecule is indicated, from low concentration to high concentration.

15. The system according to claim 14,
wherein at the first receiving opening, an intended receipt of a sample tube with a first concentration of a target molecule is indicated,
wherein the tube holding device comprises a second receiving opening at which an intended receipt of a sample tube with a second concentration of a target molecule is indicated, and
wherein the first and second receiving openings are positioned relative to each other such that straight pipetting paths from a central region to an edged region of the tube holding device are facilitated from low to high concentrations.

* * * * *